(12) United States Patent
Duesbery et al.

(10) Patent No.: US 6,911,203 B2
(45) Date of Patent: Jun. 28, 2005

(54) ANTHRAX LETHAL FACTOR IS A MAPK KINASE PROTEASE

(75) Inventors: Nicholas Duesbery, Grand Rapids, MI (US); Craig Webb, Rockford, MI (US); Stephen Leppla, Bethesda, MD (US); George Vande Woude, Ada, MI (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 274 days.

(21) Appl. No.: 10/093,200

(22) Filed: Mar. 5, 2002

(65) Prior Publication Data

US 2002/0187521 A1 Dec. 12, 2002

Related U.S. Application Data

(62) Division of application No. 09/623,104, filed as application No. PCT/US99/07126 on Mar. 31, 1999, now Pat. No. 6,485,925.
(60) Provisional application No. 60/080,330, filed on Apr. 1, 1998.

(51) Int. Cl.[7] .......................... A61K 38/46; A01N 63/00; C12N 9/52; C12N 15/63; C12Q 1/40
(52) U.S. Cl. ....................... 424/94.67; 435/220; 435/23; 435/320.1; 435/325; 435/455; 435/458; 435/387.3; 424/93.1
(58) Field of Search .......................... 435/220, 23, 325, 435/320.1, 455, 458, 387.3; 424/94.67, 93.1

(56) References Cited

U.S. PATENT DOCUMENTS 6,485,925 B1 * 11/2002 Duesbery et al. ............. 435/23

OTHER PUBLICATIONS

Pugsley A. P. Bacterial toxins deliver the good, Proc. Natl. Acad. Sci. USA, 1996, 93, 8155–8156.*
Duesbery N. S. et al., Anthrax lethal factor ccauses proteolytic inactivation of mitogen–activated protein kinase kinase, J. Appl. Microbiol., 1999, 87, 289–293.*
Liu S. et al. Targeting of Tumor Cells by Cell Surface Urokinase Plasminogen Activator–dependent Anthrax Toxin, J. Bilo. Chem 2001, 276, 17976–17984.*
Duesbery N. S. et al., Suppression of ras–mediated transformation and inhibition of tumor growth and angiogenesis by anthrax lethal factor, a proteolytic inhibitor of multiple MEK pathways, Proc. Natl. Acad. Sci. USA, 2001, 98, 4089–4094.*
Dunn F. B. Anthrax as a Cancer Drug?, J. Natl. Cancer. Inst., 2001, 93, 1680–1681.*
Koo H.–M. et al., Apoptosis and melanogenesis in human melanoma cells induced by anthrax lethal factor inactivation of mitogen–activated protein kinase kinase, Proc. Natl. Acad. Sci. USA, 2002, 99, 3052–3057.*
Oka H. et al. Constitutive activation of mitogen–activated protein (MAP) kinases in human renal cell carcinoma, Cancer Res. 1995, 18, 4182–4187.*
Duesbery, Nicholas S., et al. "Proteolytic Inactivation of MAP–Kinase–Kinase by Anthrax Lethal Factor," *Science* 280:734–737 (May 1, 1998).
Duesbery, Nick S., et al. "CENP–E is an essential kinetochore motor in maturing oocytes and is masked during Mos–dependent, cell cycle arrest at metaphase II," *Proc. Natl. Acad. Sci. USA* 94:9165–9170 (Aug. 1997).
Kimpel, Kurt R., et al. "Anthrax toxin lethal factor contains a zinc metalloprotease consensus sequence which is required for lethal toxin activity," *Molecular Microbiology* 13(6):1093–1100 (1994).
Koo, Han–Mo, et al. "Enhanced Sensitivity to 1–β–D–Arabinofuranosylcytosine and Topoisomerase II Inhibitors in Tumor Cell Lines Harboring Activated ras Oncogenes," *Cancer Research* 56:5211–5216 (Nov. 15, 1996).
Menard, Armelle, et al. "The cytotoxic activity of *Bacillus anthracis* lethal factor is inhibited by leukotriene $A_4$ hydrolase and metallopeptidase inhibitors," *Biochem. J.* 320:687–691 (1996).
Weinstein, John N., et al. "An Information–Intensive Approach to the Molecular Pharmacology of Cancer," *Science* 275:343–349 (Jan. 17, 1997).

* cited by examiner

*Primary Examiner*—Tekchand Saidha
*Assistant Examiner*—Malgorzata A. Walicka
(74) *Attorney, Agent, or Firm*—Townsend and Townsend and Crew LLP

(57) ABSTRACT

The present invention relates to in vitro and ex vivo methods of screening for modulators, homologues, and mimetics of lethal factor mitogen activated protein kinase kinase (MAPKK) protease activity, as well as methods of treating cancer by administering LF to transformed cells.

10 Claims, 1 Drawing Sheet

```
XMAPKK1   -PKKKPTPIQLNPNP----EGTAVNGTPTAETNLEALQKKLEEL-ELDEQQRKRLE-
MMAPKK1   -PKKKPTPIQLNPAP----DGSAVNGTSSAETNLEALQKKLEEL-ELDEQQRKRLED
HMAPKK1   -PKKKPTPIQLNPAP----DGSAVNGTSSAETNLEALQKKLEEL-ELDEQQRKRLE-
HMAPKK2   -LARRKPVLPALTINPTIAEGPSPTSEGASEANLVDLQKKLEEL-ELDEQQ-----
HMAPKK3   ---SKPPAPNPTPPR----NLDSRTFITIGDRNFEVEADDLVTISELGRGAYGVVE-
HMAPKK4   -AAPSPSGGGGSGGGSGSGTPGPVGSPAPGHPAVSSMQGKRKALKLNFAN-------
```

*FIG. 1.*

ANTHRAX LETHAL FACTOR IS A MAPK KINASE PROTEASE

CROSS REFERENCE TO RELATED APPLICATIONS

This application is a divisional of U.S. Ser. No. 09/623,104, filed Dec. 13, 2000, now U.S. Pat. No. 6,485,925 which claims priority to PCT/US99/07126, filed Mar. 31, 1999, and U.S. Ser. No. 60/080,330, filed Apr. 1, 1998, herein incorporated by reference in their entirety.

FEDERALLY SPONSORED RESEARCH AND DEVELOPMENT

Not applicable.

FIELD OF THE INVENTION

The present invention relates to in vitro and ex vivo methods of screening for modulators, homologues, and mimetics of lethal factor mitogen activated protein kinase kinase (MAPKK) protease activity, as well as methods of treating cancer by administering LF to tranformed cells.

BACKGROUND OF THE INVENTION

Anthrax toxin, produced by *Bacillus anthracis*, is composed of three proteins: protective antigen (PA), edema factor (EF), and lethal factor (LF) (Leppla, *Handbook of Natural Toxins* 8:543–572 (Moss et al., eds., 1995)). PA alone has no toxic effect upon cells, but instead binds to specific cell surface receptors. Upon proteolytic activation to a 63-kDa fragment (PA63), PA forms a heptameric membrane-inserted channel, which mediates the entry of EF and LF into the cytosol via the endosomal pathway (Gordon et al., *Infect. Immun.* 56:1066–1069 (1988); Milne et al., *J. Biol. Chem.* 269:20607–20612 (1994)). Thus, EF or LF are toxic to cells when combined with PA.

EF is an adenylate cyclase, and together with PA forms a toxin referred to as edema toxin (Leppla, *Proc. Natl. Acad. Sci. USA* 79:3162–3166 (1982)). LF and PA together form a toxin referred to as lethal toxin ("LT"). Until the present discovery, however, the specific activity of LF in the cell was unknown. Lethal toxin is the dominant virulence factor produced by *B. anthracis* and is the major cause of death of infected animals (Pezard et al., *Infect. Immun.* 59:3472–3477 (1991)). Intravenous injection of lethal toxin causes death of Fisher 344 rats in as little as 38 minutes (Ezzell et al., *Infect Immun.* 45:761–767 (1984)), and incubation in vitro with mouse macrophages causes lysis in 90–120 minutes (Friediander,*J. Biol. Chem.* 261:7123–7126 (1986)).

LF contains a limited sequence homology to a putative zinc-binding site at residues 686–690, HEFGH (SEQ ID NO:3), characteristic of metaloproteases (Klimpel et at., *Mol. Microbiol.* 13:1093–1100(1994)). Substitution of the H or E residues inactivates LF (e.g., as in the recombinant LF mutant E687C) (Klimpel et al, 1994, supra) and decreases its binding of zinc (Klimpel et al., 1994, supra; Kocki et al., *FEMS Microbiol. Lett.* 124:343–348 (1994)). Certain metalloprotease inhibitors also protect macrophages against lethal toxin (Klimpel et al., 1994, supra; Menard et al., *Biochem J.* 320:687–691 (1996)). However, no physiological substrate has been identified for LF, and LF protease activity has not been demonstrated.

SUMMARY OF THE INVENTION

The present invention thus identifies anthrax lethal factor (LF) as a protease, which acts as an inhibitor of the mitogen activated protein kinase (MAPK) signal transduction pathway. The present invention also identifies specific substrates for LF protease activity. For example, LF cleaves MAPK kinases 1, 2, and 3 (MEK) at specific sites in their N-termini, thereby preventing activation of MAPK (ERK2). LF is thus useful for inhibition of cancer cells that have an activated MAPK signal transduction pathway. Furthermore, the present invention provides means for assaying in vivo and in vitro for modulators and mimetics of LF, for use in treating cancer.

In one aspect, the present invention provides an in vitro method for screening modulators of lethal factor (LF) mitogen activated protein kinase kinase (MAPKK) protease activity, the method comprising the steps of: (i) providing LF in an aqueous solution, wherein the LF has MAPKK protease activity in the solution; (ii) contacting LF with substances suspected of having the ability to modulate MAPKK protease activity; and (iii) assaying for the level of LF MAPKK protease activity.

In another aspect, the present invention provides a kit for screening in vitro for modulators of lethal factor (LF) mitogen activated protein kinase kinase (MAPKK) protease activity, the kit comprising; (i) a container holding LF, wherein the LF has MAPKK protease activity; and (ii) instructions for assaying for LF MAPKK protease activity.

In another aspect, the present invention provides an in vivo method for screening modulators of lethal factor (LF) mitogen activated protein kinase kinase (MAPKK) protease activity, the method comprising the steps of: (i) contacting a living cell with LF, wherein the LF has MAPKK protease activity; (ii) contacting the cell with substances suspected of having the ability to modulate MAPKK protease activity; and (iii) assaying for the level of LF MAPKK protease activity.

In another aspect, the present invention provides an in vitro method for screening mimetics of lethal factor (LF) having mitogen activated protein kinase kinase (MAPKK) protease activity, the method comprising the steps of: (i) providing a compound suspected of being an LF mimetic in an aqueous solution; and (ii) assaying for the level of MAPKK protease activity.

In another aspect, the present invention provides an in vivo method for screening for minetics of lethal factor (LF) having mitogen activated protein kinase kinase (MAPKK) protease activity, the method comprising the steps of: (i) contacting a living cell with a compound suspected of being an LF mimetic; and (ii) assaying for the level of MAPKK protease activity.

In another aspect, the present invention provides a method for inhibiting proliferation of a cancer cell, the method comprising the step of contacting the cell with LF, wherein the LF has MAPKK protease activity.

In one embodiment, the LF is recombinant. In another embodiment, the MAPKK1 or MAPKK2 is recombinant. In another embodiment, the recombinant MAPKK1 or recombinant MAPKK2 is linked to a detectable moiety.

In one embodiment, the assay is a Mos-induced activation of MAPK assay in a *Xenopus* oocyte. In another embodiment, the assay is an MAPKK1 or MAPKK2 mobility assay. In another embodiment, the assay is an MBP phosphorylation assay.

In one embodiment, the step of contacting the cell comprising transducing the cell with an expression vector encoding LF. In another embodiment, the step of contacting further comprises contacting a cell with LF in the presence of protective antigen (PA). In another embodiment, the PA is a fusion protein targeted to the cancer cell.

In another embodiment, the mitogen activated protein kinase (MAPK) signal transduction pathway is activated in the cell.

In one embodiment, the cell is a human cell. In another embodiment, the cell is a *Xenopus* oocyte. In another embodiment, the cell is a cancer cell. In another embodiment, the cancer cell is from a sarcoma. In another embodiment, the cell is from a transformed cell line. In another embodiment, the cell line is transformed with Ras.

In another aspect, the invention provides methods for reversing a transformed phenotype in a cell by treating the cell with LT. In one embodiment, morphological changes associated with transformation are reversed. In another embodiment, the diffuse pattern of actin distribution that is characteristic of transformed cells is reversed. In another embodiment, the rate and extent of proliferation of a transformed cell is inhibited. In another embodiment, the ability of a transformed cell to grow independently of anchorage to a substrate is reversed.

In another aspect, the invention provides a method for identifying a three-dimensional structure of MAPKK or LF proteins, the method comprising the steps of: (i) receiving input of at least 10 contiguous amino acids of the amino acid sequence of MAPKK or LF, or at least 30 contiguous nucleotides of the nucleotide sequence of a gene encoding MAPKK or LF, and conservatively modified variants thereof; and (ii) generating a three-dimensional structure of the protein encoded by the amino acid sequence.

In one embodiment, the amino acid sequence is a primary structure and the generating step includes the steps of: (i) forming a secondary structure from said primary structure using energy terms encoded by the primary structure; and (ii) forming a tertiary structure from said secondary structure using energy terms encoded by said secondary structure. In another embodiment, the generating step includes the step of forming a quaternary structure from said tertiary structure using anisotropic terms encoded by the tertiary structure. Another embodiment further comprises the step of identifying regions of the three-dimensional structure of the protein that bind to ligands and using the regions to identify ligands that bind to the protein.

BRIEF DESCRIPTION OF THE DRAWINGS

FIG. 1: Alignment of the N-terminal amino acids of MAPKK 1–4. The N-terminal 60 amino acids of *Xenopus* (X) MAPKK1 (SEQ ID NQ:4), mouse (M) MAPKK1 (SEQ ID NO:5), as well as human (H) MAPKK 1–4 (SEQ ID NQS:6–9) were aligned using the Multiple Sequence Alignment tool of the Institute for Biomedical Computing, Washington University, St. Louis, accessible through the internet (http://www.ibc.wustl.edu/ibc/msa.html).

DESCRIPTION OF THE PREFERRED EMBODIMENT

I. Introduction

The present invention identifies anthrax lethal factor (LF) as an inhibitor of the mitogen activated protein kinase (MAPK) signal transduction pathway. LF specifically cleaves MAPKK, which is a kinase component of the MAPK cascade. The mitogen activated protein kinase (MAPK) signal transduction pathway is involved in cell proliferation and differentiation. This pathway also plays a crucial role in regulating oocyte meiotic maturation (Moriguchi et al., *Adv. Pharmacol.* 36:121–137 (1996); Murakami et al., *Methods in Enzymology* 283:584–600 (Dunphy, ed., 1997); Matten et al., *Seminars in Dev. Biol.* 5:173–181 (1994)).

Constitutive activation of signal transduction pathways can lead to cell transformation. The MAPK signal transduction pathway involves a cascade of kinases, in which MAPKK phosphorylates and activates MAPK, and MAPK phosphorylates and activates pp90$^{rsk}$ (see, e.g., Stugill et al., *Nature* 334:715 (1988); Gomez & Cohen, *Nature* 353:170 (1991)). In addition, cellular forms of oncogenes participate in this pathway as signalling components upstream of the MAPK phosphorylation cascade, e.g., Ras, Raf, and Mos. Furthermore, a variety of cytokines that interact with cell surface receptors have the ability to activate this pathway, e.g., IL1 and TNF. As described herein, LF and its homologues, modulators, and mimetics are thus useful for inhibiting the proliferation of cancer cells.

LF inhibits the MAPK pathway via protease activity, by cleaving its substrate, mitogen activated protein kinase kinase (MAPKK). Thus, the discovery that LF is a protease that inhibits the MAPK signal transduction pathway provides means for identifying novel therapeutic agents such as LF mimetics that inhibit the MAPK signal transduction pathway. Such agents are useful for treating cancer. Indeed, it has been discovered that LF and PA can reverse a transformed phenotype in cells. As shown in Example VII, infra, LF and PA can reverse numerous cellular properties associated with transformation, including, but not limited to, morphological features, intracellular patterns of actin distribution, proliferation rates, and anchorage-independent growth.

In addition, LF and LF mimetics that are modified to specifically target cancer cells are particularly useful as cancer therapeutics. This invention also provides means for specifically assaying for modulators of LF activity, e.g., inhibitors and activators. For example, LF inhibitors are useful as therapeutic agents for *B. anthracis* infection and inhibitors of anthrax lethal toxin. LF activators may be useful to enhance LF or LF mimetic activity for treatment of cancer. Such mimetics and modulators of LF can be identified using high throughput assay techniques, using the assays described herein.

II. Definitions

Unless defined otherwise, all technical and scientific terms used herein have the meaning commonly understood by one of ordinary skill in the art to which this invention belongs.

The "mitogen activated protein kinase (MAPK) pathway" is a signal transduction pathway that effects gene regulation, which controls cell proliferation and differentiation in response to extracellular signals. This pathway also involved in oocyte meiotic maturation. The MAPK pathway is found, e.g., in frogs, and in mammals, e.g., mice, rats, and humans. This pathway can be "activated" by cytokines such as II-1 and TNF, and constitutively activated by proteins such as Mos, Raf, Ras, and V12HaRas, (see, e.g., Moriguchi et al., *Adv. Pharmacol.* 36:121–137 (1996); Murakami & Vande Woude, in *Methods in Enzymology* 283:584–600 (Dunphy, ed., 1997); Matten & Vande Woude, *Seminars in Developmental Biol.* 5:173–181 (1994); White et al., *Cell* 80:533–541 (1995); Ruckdeschel et al., *J. Biol. Chem.* 272:15920–15927 (1997); West et al., *J. Leukoc. Biol.* 91:88–95 (1997); Winston et al., *J. Immunol.* 155:1525–1533 (1995); Hambleton et al., *J. Exp. Med.* 182:147–154 (1995); Ridley et al., *J. Immunol.* 158:3165–3173 (1997); Lu et al., *Neurochem. Int.* 30:401–410 (1997); Guan et al., *J. Biol. Chem.* 272:8083–8089 (1997); Scherle et al., *Biochem. Biophys. Res. Commun.* 230:573–577 (1997); Huwiler et al., *FEBS Lett.* 350:135–138 (1994); and Bird et al., *FEBS Lett.* 338:31–36 (1994)).

"Mitogen activated protein kinase kinase (MAPKK)" refers to a family of protein kinases that are part of the mitogen activated protein kinase (MAPK, also known as ERK) signal transduction pathway, e.g., MAPKK1, MAPKK2, MAPKK3 (also known as MEK). These proteins share sequence similarity and are cleaved near the N-terminus by LF (see FIG. 1). The term MAPKK thus refers to members of the MAPKK family, e.g., MAPKK1, MAPKK2, and MAPKK3, and conservatively modified variants thereof. The term also includes polymorphic variants, alleles, mutants and interspecies homologues with greater than about 60% sequence homology to MAPKKs 1–3 (see discussion of MAPKK Genebank deposit, below).

"Mitogen activated protein kinase kinase protease activity" (MAPKK, also known as MEK) or "LF MAPKK protease activity" refers the activity of a molecule, e.g., LF, an LF homologue, or an LF mimetic that has the ability to specifically cleave members of the MAPKK family, e.g., MAPKK1, MAPKK2, MAPKK3, at the N-terminus.

Anthrax "lethal factor" or "LF" is a protein that is naturally produced by *B. anthracis* and that has MAPKK protease activity. As used herein, the term LF includes naturally occurring LF, recombinant LF, and functional LF equivalents that have MAPKK protease activity. The term LF therefore refers to LF homologues such as polymorphic variants, alleles, mutants, and closely related interspecies variants that have about at least 60% amino acid sequence identity to LF (e.g., are substantially identical to LF; see Genebank sequence deposit, below) and have MAPKK protease activity, as determined using the assays described herein. Deletion analysis of LF shows that the PA binding domain is at the amino-terminus of LF, and that amino-terminal residues 1–254 of LF are sufficient for PA binding activity (Arora et al., *J. Biol. Chem.* 268:3334–3341 (1993)). When LF is administered with PA, LF preferably includes the PA binding domain.

An "LF mimetic" refers to a compound or molecule, e.g., a peptide, polypeptide, or small chemical molecule, that recognizes MAPKK as a substrate and cleaves MAPKK at the same site as LF. LF mimetics thus include LF homologues. LF mimetics would also include small LF peptides that retained the LF MAPKK protease active site, and conservatively modified variants thereof, as well as truncated versions of LF that retained LF MAPKK activity. Small chemical molecules that mimic the LF active site are also LF mimetics. LF mimetics are tested using assays for LF activity, e.g., MAPKK mobility assays, MOS-induced activation of MAPK in oocytes and myelin basic protein (MBP) phosphorylation, as described below. When testing for an LF mimetic, LF is typically used as a positive control for MAPKK protease activity. A relative activity value is assigned to LF, e.g., 100. Mimic activity is achieved when mimetic MAPKK protease activity relative to the control is about 25, more preferably 50–100.

One example of a potential LF mimetic is the compound PDO9859, [2-(2'-amino-3'-methoxyphenyl)-oxanaphthalen-4-one], identified as an inhibitor of the MAPK pathway (Dudley et al., *Proc. Nat'l Acad. Sci. USA* 92:7686 (1995)). A screen of the National Cancer Institute's 60 cell line in vitro anti-neoplastic drug database (Weinstein et al., *Science* 275:343 (1997); Koo et al., *Cancer Res.* 56:5211 (1996)) revealed that this compound has an activity profile that is similar to LF.

The anthrax "protective antigen" (PA) is protein produced by *Bacillus anthracis*. PA is one of two protein components of the lethal or anthrax toxin produced by *B. anthracis*. The 83 kDa PA binds at its carboxyl-terminus to a cell surface receptor, where it is specifically cleaved by a protease, e.g., furin, clostripain, or trypsin. This enzymatic cleavage releases a 20 kDa amino-terminal PA fragment, while a 63 kDa carboxyl-terminal PA fragment remains bound to the cell surface receptor. The 63 kDa fragment is also referred to as "processed protective antigen." Processed PA contains both a cell surface receptor binding site at its carboxyl-terminus and a lethal factor binding site at its new amino-terminus (see, e.g., Singh et al., *J. Biol. Chem.* 264:19103–19107 (1989)). Processed PA may be produced by enzymatic cleavage in vitro, ex vivo, or in vivo, or as a recombinant protein. As used herein the term PA refers PA molecules that have the lethal factor binding site, e.g., recombinant PA, naturally occurring PA, functional equivalents of PA that contain the lethal factor binding site, and PA fusion proteins that contain the lethal factor binding site.

As described in U.S. Pat. Nos. 5,591,631 and 5,677,274 (herein incorporated by reference in their entirety), PA fusion proteins can be made that target PA to particular cells, such as cancer cells and HIV infected cells, using PA fusion proteins comprising ligands for receptors that are specifically expressed on the target cell.

"Lethal toxin", or "LT", refers to the combination of PA and LF.

"Modulators of LF MAPKK protease activity" refers to activating or inhibitory molecules identified using in vitro and in vivo assays for LF MAPKK activity. Such assays include, e.g., MAPKK mobility assays, MOS-induced activation of MAPK in oocytes, myelin basic protein (MBP) phosphorylation, morphological changes, immortalization of cells, aberrant growth control, anchorage dependence, proliferation, malignancy, contact inhibition and density limitation of growth, growth factor or serum dependence, tumor specific markers levels, invasiveness, tumor growth, and the like, in vitro, in vivo, and ex vivo as described below. Potential modulators include peptides, polypeptides, and small chemical molecules. The ability of LF, its homologues, mimetics, and modulators to inhibit proliferation of cancer cells can also be determined using the assays described herein.

Samples or assays that are treated with a potential LF MAPKK protease modulators or LF compounds that are used to treat cancer are compared to control samples without the test compound, to examine the extent of inhibition or activation of LF MAPKK protease activity. Control samples (untreated with test inhibitors or activators) are assigned a relative LF MAPKK protease activity value of 100. Inhibition of LF MAPKK protease activity is achieved when the LF MAPKK protease activity value relative to the control is about 75, preferably 50, more preferably 25. Activation is achieved when the LF MAPKK protease activity value relative to the control is about 150, more preferably 200.

A "Mos-induced activation assay" refers to an assay for LF MAPKK protease activity that tests for inhibition of oocyte maturation after treatment with LF, typically by examining inhibition of germinal vesicle breakdown (GVBD).

A "MAPKK mobility assay" refers to an assay for LF MAPKK protease activity that tests for changes in MAPKK electrophoretic mobility after treatment with LF.

A "myelin basic protein (MBP) phosphorylation assay" refers to an assay for LF MAPKK protease activity that tests for inhibition of myelin basic protein (MBP) phosphorylation after treatment with LF.

The phrase "contacting a cell" refers to any method whereby LF, an LF homologue, modulator, or an LF mimetic is introduced into a cell, e.g., by transduction of a nucleic acid encoding LF or an LF homologue or mimetic, by administering LF in the presence of PA to the cell medium, by injecting LF or an LF homologue or mimetic into the cell, by conjugating LF or an LF homologue or mimetic to a molecule, e.g., a receptor ligand, that allows LF or the LF homologue or mimetic to be translocated into a cell, and by introducing LF or the LF homologue or mimetic into a cell using a vehicle such as a liposome.

"Transduction" refers to any method whereby a nucleic acid is introduced into a cell, e.g., by transfection, lipofection, electroporation, biolistics, passive uptake, lipid:nucleic acid complexes, viral vector transduction, injection, naked DNA, and the like.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

"In vivo" refers to assays that are performed using living cells, including cells in an animal and cells ex vivo.

"Ex vivo" refers to assays that are performed using a cell with an intact membrane that is outside of the body, e.g., explants, cultured cell lines, transformed cell lines, primary cell lines, and extracted tissue, e.g., blood, oocytes.

"In vitro" refers to assays that do not require the presence of a cell with an intact membrane.

A "cancer cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage dependence, proliferation, malignancy, contact inhibition and density limitation of growth, growth factor or serum dependence, tumor specific markers levels, invasiveness, tumor growth or suppression in suitable animal hosts such as nude mice, and the like, in vitro, in vivo, and ex vivo (see Example VII) (see also Freshney, *Culture of Animal Cells: A Manual of Basic Technique* (3rd ed. 1994)).

A "sarcoma" refers to a type of cancer cell that is derived from connective tissue, e.g., bone (osteosarcoma) cartilage (chondrosarcoma), muscle (rhabdomyosarcoma or rhabdosarcoma), fat cells (liposarcoma), lymphoid tissue (lymphosarcoma), collagen-producing fibroblasts (fibrosarcoma). Sarcomas may be induced by infection with certain viruses, e.g., Kaposi's sarcoma, Rous sarcoma virus, etc.

"Nucleic acid" refers to deoxyribonucleotides or ribonucleotides and polymers thereof in either single- or double-stranded form. The term encompasses nucleic acids containing known nucleotide analogues or modified backbone residues or linkages, which are synthetic, naturally occurring, and non-naturally occurring, which have similar binding properties as the reference nucleic acid, and which are metabolized in a manner similar to the reference nucleotides. Examples of such analogues include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

The terms "polypeptide," "peptide," and "protein" are used interchangeably herein to refer to a polymer of amino acid residues. The terms apply to amino acid polymers in which one or more amino acid residue is an analogue or mimetic of a corresponding naturally occurring amino acid, as well as to naturally occurring amino acid polymers.

The term "amino acid" refers to naturally occurring and synthetic amino acids, as well as amino acid analogues and amino acid mimetics that function in a manner similar to the naturally occurring amino acids. Naturally occurring amino acids are those encoded by the genetic code, as well as those amino acids that are later modified, e.g., hydroxyproline, alpha-carboxyglutamate, and O-phosphoserine. Amino acid analogues refers to compounds that have the same basic chemical structure as a naturally occurring amino acid, i.e., an alpha carbon that is bound to a hydrogen, a carboxyl group, an amino group, and an R group (e.g., homoserine, norleucine, methionine sulfoxide, methionine methyl sulfonium). Such analogues have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W).
(see, e.g., Creighton, *Proteins* (1984)).

A "detectable moiety" or label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins for which antisera or monoclonal antibodies are available.

A protein that is "linked to a detectable moiety" is one that is bound, either covalently, through a linker, or through ionic, van der Waals or hydrogen bonds to a label such that the presence of the protein may be detected by detecting the presence of the label or detectable moiety bound to the protein.

The term "recombinant" when used with reference, e.g., to a cell, nucleic acid, vector, or protein indicates that the cell, nucleic acid, or vector has been modified by the introduction of a heterologous nucleic acid or the alteration of a native nucleic acid, or that the cell is derived from a cell so modified, or that the protein is encoded or expressed by such a nucleic acid or cell. Thus, for example, recombinant cells express genes and proteins that are not found within the native (non-recombinant) form of the cell or express native genes and proteins that are otherwise abnormally expressed, under expressed or not expressed at all.

The terms "identical" or percent "identity," in the context of two or more nucleic acids or polypeptide sequences, refer to two or more sequences or subsequences that are the same or have a specified percentage of amino acid residues or nucleotides (i.e., 60% identity) that are the same, when compared and aligned for maximum correspondence over a comparison window, as measured using one of the following sequence comparison algorithms or by manual alignment and visual inspection. Such sequences are then said to be "substantially identical." This definition also refers to the complement of a test sequence. Preferably, the percent identity exists over a region of the sequence that is at least about 25 amino acids in length, more preferably over a region that is 50 or 100 amino acids in length.

For sequence comparison, one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nucleic Acids Res.* 12:387–395 (1984)).

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, *Proc. Natl. Acad. Sci.* USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci.* USA 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, or can be amplified by the same primer set.

III. In vitro, in vivo, and ex vivo Assays for Modulators, Homologues, and Mimetics of LF Activity The present invention provides assays to identify modulators of LF MAPKK protease activity and LF mimetics of this activity. The present invention also provides assays to determine suitable compounds for use in cancer therapeutics, e.g., LF, LF homologues and mimetics, and LF modulators. A variety of assays can be used to test the compounds of the invention; these assays examine phosphorylation, MAPKK cleavage, or oocyte maturation, e.g., ex vivo and in vitro Mos-activation of the MAPK pathway in oocytes (Example I); in vitro and ex vivo phosphorylation of myelin basic protein (MBP) or MAPK (Examples I and III);, ex vivo and in vitro cleavage of MAPKK and determination of electrophoretic mobility (Examples II, IV, and V), ex vivo alteration of phenotypic characteristics of transformed cells (Example VII); and other phenotypic changes in transformed or cancer cells, such as the ability to grow on soft agar; changes in contact inhibition and density limitation of growth; changes in growth factor or serum dependence; changes in the level of tumor specific markers; changes in invasiveness into Matrigel; changes in tumor growth in vivo, such as in transgenic mice, etc.

As a general assay format, samples that are with treated LF or LF homologues or mimetics and with potential LF inhibitors or activators are compared to control samples without the test compound, to examine the extent of modulation. Control samples (untreated with activators or inhibitors) are assigned a relative LF activity value of 100. Inhibition of LF is achieved when the LF activity value relative to the control is about 75, preferably 50, more preferably 25. Activation of LF is achieved when the LF activity value relative to the control is about 150, preferably 200 or higher. Activation is achieved when the LF MAPKK protease activity value relative to the control is about 150, more preferably 200. Inactive mutants of LF, e.g., LF E687C can be used as negative controls for LF activity, while LF is typically used as a positive control.

As a general assay format for LF mimetics and homologues, potential mimetics and homologues are tested using assays for LF activity, e.g., MAPKK mobility or cleavage assays, Mos-induced activation of the MAPK pathway in oocytes and myelin basic protein (MBP) or MAPK phosphorylation, as described below. When testing for an LF mimetic or homologue, LF is typically used as a positive control for MAPKK protease activity. A relative activity value is assigned to LF, e.g., 100. Mimic activity is achieved when mimetic or homologue MAPKK protease activity relative to the control is about at least 25, more preferably 50–100, or above 100, e.g., 500.

A. In vivo and ex vivo Assays for Modulators, Homologues, and Mimetics of LF

In vivo and ex vivo assays can be used to identify modulators of LF MAPKK protease activity or LF mimetics and homologues. The assays of the invention used, e.g., oocytes, in which Mos activation of the MAPK pathway is examined, or transformed cells that have activated MAPK pathways. These transformed cells typically express naturally occurring MAPKK, although they may also express recombinant MAPKK. The transformed cells or oocytes may be contacted with naturally occurring LF, recombinant LF, or LF homologues or mimetics, or the cells can express recombinant LF or recombinant LF homologues and mimetics, as described below. As described below, modulators, LF homologues, and LF mimetics are peptides, proteins, and small chemical molecules.

MAPKK, LF, and LF homologues and mimetics can be administered to a transformed cell or oocyte, e.g., by transduction with an expression vector encoding MAPKK, LF or an LF homologue or mimetic; by injection of MAPKK, LF or an LF homologue or mimetic; by administering MAPKK, LF or an LF homologue or mimetic in a liposome; by creating a targeted fusion protein with MAPKK, LF or an LF homologue or mimetic; and by contacting a cell, in the presence of PA, with LF or an LF homologue or mimetic that has the ability to bind to PA. When a cell is contacted with LF in the presence of PA, the PA binds to its cellular receptor, binds to LF, then internalizes LF into the cell. PA fusion proteins can also be used to introduce LF in cells. Such PA fusion proteins need only retain the LF binding site on PA, while the portion of PA that binds to its cellular receptor can be replaced by another cellular ligand. The fusion proteins can be targeted to a variety of cellular receptors (see, e.g., U.S. Pat. Nos. 5,677,274 and 5,591,631). In particular, such fusion proteins are useful for targeting LF to cancer cells, for inhibition of the MAPK pathway.

When assaying for LF modulators and LF mimetics, the test compounds are added in test concentrations to the cell or oocyte, as described above. For example, modulators can be added to cell media in aqueous solutions or organic solvents such as DMSO, for cellular uptake. Modulators and mimetics can also be administered by injection, by fusion proteins, by liposome delivery, by viral transduction, by transfection, by expression vectors, etc.

In oocytes, synthesis of Mos activates the MAPK pathway. Insulin also activates the MAPK pathway. This pathway is essential for activation of maturation promoting factor (MPF) and the resumption of meiosis, i.e., maturation. Oocytes can be isolated from any convenient source according to standard methods, e.g., frog, fish, or mammalian, e.g., mouse or bovine oocytes. After LF or an LF homologue or mimetic is introduced to the oocytes, optionally with a modulator, the oocytes are induced to mature, e.g., for *Xenopus* oocytes, with progesterone or insulin, for fish oocytes, with dihydroxyprogesterone. Mammlian oocytes do not need induction as they spontaneously mature upon isolation. Alternatively, recombinant or naturally occurring Mos can be injected into the oocyte to activate the MAPK pathway. The oocytes are then cultured according to standard conditions (see, e.g., Duesbery et al., *Proc. Natl. Acad. Sci. USA* 94:9165–9170 (1997); see also Freshney, *Culture of Animal Cells, A Manual of Basic Technique* (3rd ed. 1994)).

LF modulators, homologues, and mimetics can be assayed by examining inhibition of germinal vesicle breakdown (GVBD) (see, e.g., Example I). An intact germinal vesicle signals that maturation, and the MAPK pathway, has been inhibited. Inhibition of GVBD is determined by visual inspection of the oocytes (using a microscope) for the presence of the germinal vesicle. The germinal vesicle is seen as a white spot on one side of the oocyte. Inhibition of GVBD can be confirmed by fixing oocytes and manually dissecting to examine whether the germinal vesicle is intact.

Alternatively, LF modulators, homologues, and mimetics can be identified by phosphorylation of MAPKK substrates, such MAPK. In such assays, oocytes are lysed, and the oocyte lysates are subjected to electrophoresis, and western blots are probed with specific antibodies against phosphorylated MAPK. The oocyte lysates can also be examined using ELISA techniques. Optionally, cells can be probed with specific antibodies using in situ techniques.

In addition, cleavage of MAPKK by LF can be directly detected, using specific antibodies to the truncated MAPKK or by examining increased electrophoretic mobility with antibodies to the MAPKK C-terminus. In such assays, oocytes are lysed, and the oocyte lysates are subjected to electrophoresis, and western blots are probed with a suitable antibody to detect truncated MAPKK. Alternatively, the oocyte lysates are examined using ELISA techniques. Oocytes can also be labeled in situ with antibodies that recognize truncated MAPKK.

Transformed cell lines can also be used ex vivo to identify LF modulators, homologues, and mimetics (see, e.g., Example II and Example VII). The MAPK pathway in the transformed cells can be activated by treatment with cytokines such as IL1 and TNF-α, as well as other cytokines known to those of skill in the art. Alternatively, cell lines that have a constitutively activated MAPK pathway can be used. For example, such cells include cell lines in which the MAPK pathway is activated as a result of upstream signalling by oncogenes such as Met, Ras, Raf and Mos, e.g., NIH 3T3 (490) cells, which express the V12HaRas oncogene, IHKE cells transformed with Ras, and NIH3T3 cells transformed with activated Met. Tumor cell lines or tumor explants with activated MAPK pathways can also be used in the assays of the invention, e.g., carcinomas and sarcomas such as osteosarcomas, chondrosarcomas, rhabdomyosarcomas, liposarcomas, lymphosarcomas, and fibrosarcomas. Sarcomas may be induced by infection with certain viruses, e.g., Kaposi's sarcoma, Rous sarcoma virus, etc.

LF modulator, homologue, or LF mimetic activity can be examined these ex vivo assays by direct detection of MAPKK cleavage. MAPKK cleavage or inhibition of MAPKK cleavage can be detected by any suitable means, as described above. For example, cells can be labeled in situ with antibodies that specifically recognize cleaved MAPKK. Alternatively, the cells are lysed and the cellular protein is examined using a number of assays, e.g., ELISAs with antibodies specific for truncated MAPKK or western blots with C-terminal MAPKK antibodies, to detect MAPKK with altered electrophoretic mobility. Cleavage of MAPKK can also be indirectly monitored by examining phosphorylation of MAPKK substrates such as MAPK, as described above, using specific antibodies.

The following are additional assays that can be used to identify compounds such as LF, LF homologues, LF mimetics, and LF modulators, which are capable of regulating cell proliferation and tumor suppression. The phrase "LF constructs" can refer to any of LF and its alleles, interspecies homologues, polymorphic variants and mutants, as well as LF mimetics, as used herein. Functional LF homologues, mimetics, and modulators identified by the following assays can then be used in gene therapy to inhibit abnormal cellular proliferation and transformation.

Soft Agar Growth or Colony Formation in Suspension

Normal cells require a solid substrate to attach and grow. When the cells are transformed, they lose this phenotype and grow detached from the substrate. For example, transformed cells can grow in stirred suspension culture or suspended in semi-solid media, such as semi-solid or soft agar. The transformed cells, when transfected with LF, regenerate normal phenotype and require a solid substrate to attach and grow.

Soft agar growth or colony formation in suspension assays can be used to identify LF homologues, mimetics, and modulators, which when expressed in host cells, inhibit abnormal cellular proliferation and transformation. Typically, transformed host cells (e.g., cells that grow on soft agar) are used in this assay. Expression of LF in these transformed host cells would reduce or eliminate the host cells' ability to grow in stirred suspension culture or suspended in semi-solid media, such as semi-solid or soft. This is because the host cells would regenerate anchorage dependence of normal cells, and therefore require a solid substrate to grow. Therefore, this assay can be used to identify LF constructs which reverse the transformed cell phenotype. Once identified, such LF constructs and compounds can be used in gene therapy to inhibit abnormal cellular proliferation and transformation.

Techniques for soft agar growth or colony formation in suspension assays are described in Freshney, *Culture of Animal Cells a Manual of Basic Technique,* 3$^{rd}$ ed., Wiley-Liss, New York (1994), herein incorporated by reference. See also, the methods section of Garkavtsev et al. (1996), supra, herein incorporated by reference.

Contact Inhibition and Density Limitation of Growth

Normal cells typically grow in a flat and organized pattern in a petri dish until they touch other cells. When the cells touch one another, they are contact inhibited and stop growing. When cells are transformed, however, the cells are not contact inhibited and continue to grow to high densities in disorganized foci. Thus, the transformed cells grow to a higher saturation density than normal cells. This can be detected morphologically by the formation of a disoriented monolayer of cells or rounded cells in foci within the regular pattern of normal surrounding cells. Alternatively, labeling index with [$^3$H]-thymidine at saturation density can be used to measure density limitation of growth. See Freshney (1994), supra. The transformed cells, when transfected with LF, regenerate a normal phenotype and become contact inhibited and would grow to a lower density.

Contact inhibition and density limitation of growth assays can be used to identify LF constructs which are capable of inhibiting abnormal proliferation and transformation in host cells. Typically, transformed host cells (e.g., cells that are not contact inhibited) are used in this assay. Expression of an LF construct in these transformed host cells would result in cells which are contact inhibited and grow to a lower saturation density than the transformed cells. Therefore, this assay can be used to identify LF constructs which function as cancer therapeutics. Once identified, such LF constructs can be used in gene therapy to inhibit abnormal cellular proliferation and transformation.

In this assay, labeling index with [$^3$H]-thymidine at saturation density is a preferred method of measuring density limitation of growth. Transformed host cells are transfected with an LF construct and are grown for 24 hours at saturation density in non-limiting medium conditions. The percentage of cells labeling with [$^3$H]-thymidine is determined autoradiogrpahically. See, Freshney (1994), supra. The host cells expressing a functional LF construct would give arise to a lower labeling index compared to control (e.g., transformed host cells transfected with a vector lacking an insert).

Growth Factor or Serum Dependence

Growth factor or serum dependence can be used as an assay to identify functional LF constructs. Transformed cells have a lower serum dependence than their normal counterparts (see, e.g., Temin, *J. Natl. Cancer Insti.* 37:167–175 (1966); Eagle et al., *J. Exp. Med.* 131:836–879 (1970)); Freshney, supra. This is in part due to release of various growth factors by the transformed cells. When an LF gene is transfected and expressed in these transformed cells, the cells would reacquire serum dependence and would release growth factors at a lower level. Therefore, this assay can be used to identify LF constructs which function as cancer therapeutics. Growth factor or serum dependence of transformed host cells which are transfected with an LF construct can be compared with that of control (e.g., transformed host cells which are transfected with a vector without insert). Host cells expressing a functional LF would exhibit an increase in growth factor and serum dependence compared to control.

Tumor Specific Markers Levels

Tumor cells release an increased amount of certain factors (hereinafter "tumor specific markers") than their normal counterparts. For example, plasminogen activator (PA) is released from human glioma at a higher level than from normal brain cells (see, e.g., Gullino, *Angiogenesis, tumor vascularization, and potential interference with tumor growth*. In Mihich (ed.): "Biological Responses in Cancer." New York, Academic Press, pp. 178–184 (1985)). Similarly, Tumor angiogenesis factor (TAF) is released at a higher level in tumor cells than their normal counterparts. See, e.g., Folkman, Angiogenesis and cancer, *Sem Cancer Biol.* (1992)).

Tumor specific markers can be assayed for to identify LF constructs, which when expressed, decrease the level of release of these markers from host cells. Typically, transformed or tumorigenic host cells are used. Expression of the LF gene in these host cells would reduce or eliminate the release of tumor specific markers from these cells. Therefore, this assay can be used to identify LF constructs for treatment of cancer.

Various techniques which measure the release of these factors are described in Freshney (1994), supra. Also, see, Unkless et al., *J. Biol. Chem.* 249:4295–4305 (1974); Strickland & Beers, *J. Biol. Chem.* 251:5694–5702 (1976); Whur et al., *Br. J. Cancer* 42:305–312 (1980); Gulino, *Angiogenesis, tumor vascularization, and potential interference with tumor growth*. In Mihich, E. (ed): "Biological Responses in Cancer." New York, Plenum (1985); Freshney *Anticancer Res.* 5:111–130 (1985).

Invasiveness into Matrigel

The degree of invasiveness into Matrigel or some other extracellular matrix constituent can be used as an assay to identify LF constructs which are capable of inhibiting abnormal cell proliferation and tumor growth. Tumor cells exhibit a good correlation between malignancy and invasiveness of cells into Matrigel or some other extracellular matrix constituent. In this assay, tumorigenic cells are typically used as host cells. Expression of an LF gene in these host cells would decrease invasiveness of the host cells. Therefore, functional LF constructs can be identified by measuring changes in the level of invasiveness between the host cells before and after the introduction of LF constructs. If an LF construct functions as a cancer therapeutic, its expression in tumorigenic host cells would decrease invasiveness.

Techniques described in Freshney (1994), supra, can be used. Briefly, the level of invasion of host cells can be measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$I and counting the radioactivity on the distal side of the filter or bottom of the dish. See, e.g., Freshney (1984), supra.

Tumor Growth in vivo

Effects of LF on cell growth can be tested in immune-suppressed mice. Various immune-suppressed or immune-deficient host animals can be used in these assays. For example, genetically athymic "nude" mouse (see, e.g., Giovanella et al., *J. Natl. Cancer Inst.* 52:921 (1974)), a SCID mouse, a thymectomized mouse, or an irradiated mouse (see, e.g., Bradley et al., *Br. J. Cancer* 38:263 (1978); Selby et al., *Br. J. Cancer* 41:52 (1980)) can be used as a host. Transplantable tumor cells (typically about $10^6$ cells) injected into isogenic hosts will produce invasive tumors in a high proportions of cases, while normal cells of similar origin will not. In hosts which developed invasive tumors, cells expressing an LF construct are injected subcutaneously. After a suitable length of time, preferably 4–8 weeks, tumor growth is measured (e.g., by volume or by its two largest dimensions) and compared to the control. Tumors that have statistically significant reduction (using, e.g., Student's T test) are said to have inhibited growth. Using reduction of tumor size as an assay, functional LF constructs which are capable of inhibiting abnormal cell proliferation can be identified.

B. In vitro Assays for Identification of LF Modulators and Mimetics

LF homologues, modulators and mimetics can also be identified using in vitro assays. Such assays are conveniently used for high throughput screening of modulators and mimetics. For the in vitro assays of the invention, recombinant or naturally occurring LF, PA, and MAPKK can be used. For example, recombinant LF can be used in combination with a cell extract that has an activated MAPK pathway, e.g., a Mos-activated oocyte lysate, or a Ras/Raf transformed NIH3T3 cell lysate, or any of the other cells described above. In such assays, direct cleavage of MAPKK can be detected, or phosphorylation of MAPKK substrates can be examined. Alternatively, recombinant or naturally occurring MAPKK and LF or LF homologues or mimetics are incubated together under standard reaction conditions, for direct detection of MAPKK cleavage. In another assay, recombinant or naturally occurring MAPKK and LF or an LF homologue or mimetic are incubated with an MAPKK substrate such as MBP and/or MAPK, and phosphorylation of the substrate is examined.

The mimetics or modulators are added to the in vitro assays in test concentrations, by any suitable means. Typically, the modulators or mimetics are added to the assays in aqueous solutions, or in organic solvents such as DMSO.

In one assay, oocyte extracts are examined for inhibition of Mos-activation of the MAPK pathway. Purified (recombinant or naturally occurring) Mos is added to the extract, along with LF or an LF mimetic, and/or a modulator, under suitable reaction conditions (see, e.g., Example I). LF modulator or mimetic is examined by direct detect of MAPKK cleavage, using ELISA or western blots, as described above, or by examining phosphorylation of MAPKK substrates such as MAPK, using ELISA or western blots, as described above.

In another assay, extracts from cells with activated MAPK pathways are examined. Purified (recombinant or naturally occurring) LF or LF mimetic, and optionally an LF modulator, are added to the extract. LF modulator or mimetic activity is examined by direct detect of MAPKK cleavage, using ELISA or western blots, as described above, or by examining phosphorylation of MAPKK substrates such as MAPK, using ELISA or western blots, as described above.

In vitro assays can also be performed without cell extracts, by direct incubation of LF or an LF mimetic and MAPKK, or by incubation of LF or an LF mimetic and MAPKK with an MAPKK substrate. LF modulators are optionally added to such assays. After LF or an LF homologue or mimetic and MAPKK are incubated together under suitable reaction conditions (see, e.g., Example IV). MAPKK cleavage is detected by using ELISA, western blots, or direct staining of SDS-PAGE gels. MAPKK cleavage can be examined by using antibodies that specifically detect the truncated MAPKK, or by using antibodies to the C-terminus of MAPKK and detecting altered electrophoretic mobility. Altered electrophoretic mobility can also be detected by direct staining of gels.

Phosphorylation of an MAPKK substrate can also be used as an assay for LF activity and MAPKK cleavage. For example, LF or an LF mimetic, MAPKK, MAPK, and myelin basic protein (MBP) are incubated together in a kinase buffer, optionally with an LF modulator (see, e.g., Example III). Phosphorylation of either MAPK or MBP can be detected by western blot or ELISA with specific antibodies to phosphorylated MAPK or MBP protein. Alternatively, $\gamma$-$^{32}$P-ATP can be added to the kinase reaction, and direct labeling of the proteins can be examined by electrophoresis and autoradiography.

C. LF Modulators, Homologues, and Mimetics

New chemical or recombinant LF mimetics, homologues, and modulators are generated by identifying compounds with LF MAPKK protease activity or the ability to modulate LF MAPKK protease activity, using the assays described above. These compounds are often referred to as lead compounds. Once a lead compound is identified, variants are typically created and evaluated for use as a therapeutic agent. An example of an LF mimetic is a small peptide containing the LF MAPKK protease active site, or a small chemical molecule that has the same chemical structure as the LF active site. An example of an LF homologue is a naturally-occurring or recombinant variant of LF that has increased stability or increased activity. An example of an LF modulator is a small chemical or peptide that inhibits or activates LF MAPKK protease activity.

A wide variety of LF homologues can be tested for LF MAPKK protease activity, e.g., conservative modifications, truncations, targeted fusion proteins, etc. Such molecules are typically isolated from naturally occurring strains of *B. anthracis*, or made using standard recombinant technology, described below, or designed by computer assisted drug design, described below. For example, the LF MAPKK protease active site can be identified using computer assisted drug design, by site-directed mutagenesis of conserved LF domains, by screening nested deletions or by screening linker scanner deletions of LF. The LF active site and conserved domains can also be identified by comparing the amino acid sequences of LF alleles. LF homologues can then be designed that include the essential components of the active site and are conservatively modified in other regions. Standard recombinant techniques are typically used to make LF homologues, e.g., site-directed mutagenesis, random mutagenesis, nested deletions, linker scanner deletions, truncations, fusions, isolation of alleles from different *B. anthracis* strains, etc.

Combinatorial libraries also provide a source of potential LF homologues, modulators, and mimetics, particularly mimetics and modulators. In one embodiment, a library containing a large number of potential therapeutic compounds (candidate compounds) is provided. Such "combinatorial chemical libraries" are then screened in one or more LF MAPKK protease activity assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991); Houghton et al., *Nature* 354:84–88 (1991)). Peptide synthesis is by no means the only approach envisioned and intended for use with the present invention. Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with a β-D-glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries, peptide nucleic acid libraries (see, e.g., U.S. Pat. No. 5,539,083), antibody libraries (see, e.g., Vaughn et al., *Nature Biotechnology,* 14(3):309–314 (1996) and PCT/US96/10287), carbohydrate libraries (see, e.g., Liang et al., *Science,* 274:1520–1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

D. High Throughput Methodology

Any of the assays for compounds that modulate or mimic LF MAPKK protease activity, described herein, are amenable for use in high throughput screening. High throughput assays for the activity of a particular product, e.g., LF or LF mimetics or homologues, are well known to those of skill in the art. In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high thruput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

Such high throughput assays often incorporate solid substrates such as a membrane (e.g., nitrocellulose or nylon), a microtiter dish (e.g., PVC, polypropylene, or polystyrene), a test tube (glass or plastic), a dipstick (e.g., glass, PVC, polypropylene, polystyrene, latex, and the like), a microcentrifuge tube, or a glass, silica, plastic, metallic or polymer bead or other substrate such as paper.

Often in the assays of the invention, a molecule such as MAPKK is labeled with a detectable moiety. For example, in electrophoretic mobility assays, MAPKK can be labeled at the C-terminus or N-terminus (to observe cleavage by LF).

The particular label or detectable group used in the assay is not a critical aspect of the invention, as long as it does not significantly interfere with LF activity. Such detectable labels have been well-developed in the field of immunoassays and, in general, most any label useful in such methods can be applied to the present invention. A wide variety of labels may be used, with the choice of label depending on sensitivity required, ease of conjugation with the compound, stability requirements, available instrumentation, and disposal provisions.

Suitable labels are any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. Non-radioactive labels are often attached by indirect means. For example, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize the LF substrate, or secondary antibodies that recognize anti-LF-substrates.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

E. Computer Assisted Drug Design

Yet another assay for compounds that modulate LF MAPKK protease activity involves computer assisted drug design, in which a computer system is used to generate a three-dimensional structure of a protein based on the structural information encoded by the amino acid sequence. The three dimensional structure of the protein is then used to identify potential ligands that bind to the protein, or to identify molecules that are mimetics of the protein of interest. For example, the three-dimensional structure of LF can be used to identify LF mimetics and modulators that bind to LF. The structure can also be used to identify the LF protease active site. Similarly, the three-dimensional structure of MAPKK can be used to identify LF mimetics that bind to MAPKK, or LF modulators that bind to MAPKK, particularly near the N-terminus where LF cleaves MAPKK. In the computer system, the input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., MAPKK or LF. These regions are then used to identify ligands that bind to the protein of interest, or regions where LF interacts with MAPKK, or the regions where MAPKK interacts with LF.

The three-dimensional structural model of the protein is generated by entering channel protein amino acid sequences of at least 10 amino acid residues or corresponding nucleic acid sequences encoding LF or MAPKK into the computer system. The amino acid sequence represents the primary sequence or subsequence of the protein, which encodes the structural information of the protein. The sequence is entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of LF or MAPKK is then generated by the interaction of the amino acid sequence and the computer system, using software known to those of skill in the art.

The amino acid sequence represents a primary structure that encodes the information necessary to form the secondary and tertiary structure of LF or MAPKK. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the LF or MAPKK protein to identify ligands that bind to LF or MAPKK. Binding affinity between the protein and ligands is determined using energy terms to determine which ligands have an enhanced probability of binding to the protein.

IV. How to Make Recombinant LF, PA, and MAPKK Proteins

As described above, naturally occurring or recombinant LF and MAPKK and homologues and mimetics thereof can be used in the assays of the invention. Recombinant LF and MAPKK are conveniently used for in vitro assays. In addition, recombinant LF homologues and fusion proteins can be prepared for testing as LF mimetics and potential therapeutic agents. The preparation of recombinant LF, MAPKKs and PA is described below, as well as methods for isolating naturally occurring proteins.

A. General Recombinant DNA Methods

Often, recombinant proteins are used in the assays of the present invention, e.g., recombinant LF, PA, and MAPKK, mutants thereof, and functional equivalents. For producing recombinant proteins, this invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding LF, MAPKK, and PA In general, the nucleic acid sequences encoding LF, MAPKK, PA, and related nucleic acid sequence homologues are cloned from cDNA and genomic DNA libraries or isolated using amplification techniques with oligonucleotide primers. For example, LF and PA sequences are typically isolated from *B. anthracis* nucleic acid (genomic or cDNA) libraries, while genes for MAPKKs (e.g., MAPKK1, MAPKK2, etc.) can be cloned from mammalian libraries, preferably human libraries. For example, MAPKKs sequences can be isolated from sarcoma libraries with an activated MAPK pathway.

Amplification techniques using primers can also be used to amplify and isolate LF, PA, and MAPKK from DNA or RNA (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of LF directly from mRNA, from cDNA, from genomic libraries or cDNA libraries, and from plasmids. Degenerate oligonucleotides can be designed to amplify homologues. For example, the following primers can also be used to amplify a sequence of LF: 5' CCT AAG GGC ACA GCA AAG AAT GAG 3' (SEQ ID NO:1) and 5' GTG TGG CGA AAG TGG TGG TC 3' (SEQ ID NO:2). These primers can be used, e.g., to amplify a probe of several hundred nucleotides, which is then used to screen a human libraxy for full-length LF. Alternatively, the nucleic acid for LF can be directly amplified. Similar procedures can be used to isolate sequences encoding PA and MAPKK.

Nucleic acids encoding LF, PA, and MAPKK can also be isolated from expression libraries using antibodies as probes. Such polyclonal or monoclonal antibodies can be raised using recombinant or naturally occurring LF, PA, or MAPKK as antigens.

Synthetic oligonucleotides can be used to construct recombinant LF genes for use as probes, for expression of protein, and for construction of polymorphic variants or mutants such as deletion mutants. This method is performed using a series of overlapping oligonucleotides usually 40–120 bp in length, representing both the sense and nonsense strands of the gene. These DNA fragments are then annealed, ligated and cloned.

Polymorphic variants, alleles, and interspecies homologues that are substantially identical to LF, PA, or MAPKK can be isolated using LF, PA, and MAPKK nucleic acid probes and oligonucleotides under stringent hybridization conditions, by screening libraries using probes, or using amplification techniques as described above. Alternatively, expression libraries can be used to clone polymorphic variants, alleles, and interspecies homologues, by detecting expressed homologues immunologically with antisera or purified antibodies, which also recognize and selectively bind to the homologue.

The gene encoding LF has been cloned and sequenced, and has been assigned Genebank accession no. M29081 (Robertson & Leppla, *Gene* 44:71–78 (1986); Bragg & Robertson, *Gene* 81:45–54 (1989); see also U.S. Pat. Nos. 5,591,631, 5,677,274; see generally Leppla, *Anthrax Toxins, in Bacterial Toxins and Virulence Factors in Disease* (Moss et al., eds., 1995)). The gene encoding PA has been cloned and sequenced, and assigned Genebank accession no. M22589 (Irvins & Welkos, *Infect. Immun.* 54:537–542 (1986); Welkos et al., *Gene* 69:287–300 (1988); see also U.S. Pat. Nos. 5,591,631, 5,677,274; see generally Leppla, *Anthrax Toxins, in Bacterial Toxins and Virulence Factors in Disease* (Moss et al., eds., 1995)). The gene encoding, e.g., MAPKK1 and MAPKK2 have been cloned and sequenced. MAPKK1 has been assigned Genebank accession no. L11284, and the accession no. for MAPKK2 is L11285 (see, e.g., Zheng & Guan, *J. Biol. Chem.* 268:11435–11439 (1993)).

The nucleic acids of interest are typically cloned into intermediate vectors before transformation into prokaryotic or eukaryotic cells for replication and/or expression. These intermediate vectors are typically prokaryote vectors, e.g., plasmids, or shuttle vectors, as described below.

C. Expression in Prokaryotes and Eukaryotes

To obtain high level expression of a cloned gene, such as those cDNAs encoding LF, PA, and MAPKK, one typically subclones the nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the LF protein are available in, e.g., *E. coli*, Bacillus sp., and *Salmonella* (Palva et al., *Gene* 22:229–235 (1983); Mosbach et al., *Nature* 302:543–545 (1983)). Kits for such expression systems are commercially available. Eukaryotic expression systems for mammalian cells, yeast, and insect cells are well known in the art and are also commercially available.

The promoter used to direct expression of a heterologous nucleic acid depends on the particular application and is not critical. Exemplary promoters include the SV40 early promoter, SV40 later promoter, metallothionein promoter, murine mammary tumor virus promoter, Rous sarcoma virus promoter, polyhedrin promoter, or other promoters shown effective for expression in eukaryotic cells, as well as prokaryotic promoters. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the nucleic acid in host cells. A typical expression cassette thus also contains signals required for efficient polyadenylation of the transcript, ribosome binding sites, and translation termination. The nucleic acid sequence encoding the gene of choice may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

Additional elements that are typically included in expression vectors also include a replicon that functions in *E. coli*, a gene encoding antibiotic resistance to permit selection of bacteria that harbor recombinant plasmids, unique restriction sites in nonessential regions of the plasmid to allow insertion of eukaryotic sequences. In addition, some expression systems have markers that provide gene amplification such as thymidine kinase, hygromycin B phosphotransferase, and dihydrofolate reductase. The particular antibiotic resistance gene chosen is not critical, any of the many resistance genes known in the art are suitable.

The prokaryotic sequences are preferably chosen such that they do not interfere with the replication of the DNA in eukaryotic cells, if necessary.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Other exemplary eukaryotic vectors include pMSG, pAV009/A$^+$, pMTO10/A$^+$, pMAMneo-5, baculovirus pDSVE. Tags can also be added to recombinant proteins to provide convenient methods of isolation, e.g., c-myc, or hexahistidine.

Standard transfection methods are used to produce bacterial, mammalian, yeast or insect cell lines that express large quantities of LF protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher, ed., 1990)). Transformation of eukaryotic and prokaryotic cells are performed according to standard techniques, e.g., calcium phosphate transfection, polybrene, protoplast fusion, electroporation, liposomes, microinjection, plasma vectors, viral vectors (see, e.g., Morrison, *J. Bact.* 132:349–351 (1977); Clark-Curtiss & Curtiss, *Methods in Enzymology* 101:347–362 (Wu et al., eds, 1983).

After the expression vector is introduced into the cells, the transfected cells are cultured under conditions favoring expression of the gene of choice, which is recovered from the culture using standard techniques identified below.

V. Purification of LF, PA and MAPKK and Cellular Expression

Naturally occurring or recombinant LF, PA, and MAPKK can be purified for use in the assays of the invention. Naturally occurring LF and PA are purified, e.g., from *B. anthracis* Sterne (Leppla, *Production and Purification of Anthrax Toxin, Methods Enzymol.* 165:103–116 (1988); Quinn et al., Biochem J. 252:753–758 (1988)). Naturally occurring MAPKK is purified from transformed mammalian cell lines. Recombinant LF, PA, and MAPKK are purified from any suitable expression system.

LF, PA, and MAPKK may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant proteins are purified. For example, proteins having established molecular adhesion properties can be reversible fused to the protein of choice. With the appropriate ligand, the protein can be selectively adsorbed to a purification column and then freed from the column in a relatively pure form. The fused protein is then removed by enzymatic activity. Finally, the protein of choice can be purified using affinity or immunoaffinity columns.

A. Purification of Protein from Recombinant Bacteria

Recombinant proteins are expressed by transformed bacteria in large amounts, typically after promoter induction; but expression can be constitutive. Promoter induction with IPTG is a one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of recombinant inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Other suitable buffers are known to those skilled in the art. The protein of choice is separated from other bacterial proteins by standard separation techniques, e.g., with Ni-NTA agarose resin.

Alternatively, it is possible to purify the recombinant protein from bacteria periplasm. After lysis of the bacteria, when the recombinant protein is exported into the periplasm of the bacteria, the periplasmic fraction of the bacteria can be isolated by cold osmotic shock in addition to other methods known to skill in the art. To isolate recombinant proteins from the periplasm, the bacteria are centrifuged and the pellet is resuspended in ice-cold 5 mM $MgSO_4$ and kept in an ice bath for approximately 10 minutes, for cell lysis to occur. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Recombinant and Naturally Occurring Proteins Solubility Fractionation Often as an initial step, particularly if the protein mixture is complex, an initial salt fractionation can separate many of the unwanted host cell proteins (or proteins derived from the cell culture media) from the protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the protein of choice can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The protein of choice can also be separated from other proteins on the basis of its size, net surface charge, hydrophobicity, and affinity for ligands. In addition, antibodies raised against recombinant or naturally occurring proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech). For example, LF can be purified using a PA63 heptamer affinity column (Singh et al., *J. Biol. Chem.* 269:29039–29046 (1994)).

VI. Kits

The present invention also provides for kits for screening for modulators of LF. Such kits can be prepared from readily available materials and reagents. For example, such kits can comprise any one or more of the following materials: biologically active LF, reaction tubes, and instructions for testing LF activity. A wide variety of kits and components can be prepared according to the present invention, depending upon the intended user of the kit and the particular needs of the user. For example, the kit can be tailored for ex vivo or in vitro Mos-activation of MAPK, in vitro phosphorylation of MBP, ex vivo or in vitro cleavage of MAPKK and determination of electrophoretic mobility.

VII. Gene Therapy

The present invention provides the nucleic acids of LF and LF homologues for the transfection of cells in vitro and in vivo. These nucleic acids can be inserted into any of a number of well known vectors for the transfection of target cells and organisms as described below. The nucleic acids are transfected into cells, ex vivo or in vivo, through the interaction of the vector and the target cell. The nucleic acids encoding LF and LF homologues, under the control of a promoter, then expresses an LF of the present invention, thereby providing a therapeutic reagent to a cancer cell.

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808–813 (1992); Nabel & Felgner, TIBTECH 11:211–217 (1993); Mitani & Caskey, TIBTECH 11:162–166 (1993); Mulligan, *Science* 926–932 (1993); Dillon, TIBTECH 11:167–175 (1993); Miller, *Nature* 357:455–460 (1992); Van Brunt, *Biotechnology* 6(10): 1149–1154 (1998); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* (Doerfler & Böhm eds., 1995); and Yu et al., *Gene Therapy* 1: 13–26 (1994)).

Delivery of the gene or genetic material into the cell is the first critical step in gene therapy treatment of disease. A large number of delivery methods are well known to those of skill in the art. Preferably, the nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808–813 (1992); Nabel & Feigner, TIBTECH 11:211–217 (1993); Mitani & Caskey, TIBTECH 11:162–166 (1993); Dillon, TIBTECH 11:167–175 (1993); Miller, *Nature* 357:455–460 (1992); Van Brunt, *Biotechnology* 6(10):1149–1154 (1988); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* Doerfier and Böhm (eds) (1995); and Yu et al., *Gene Therapy* 1:13–26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404–410 (1995); Blaese et al., *Cancer Gene Ther.* 2:291–297 (1995); Behr et al., *Bioconjugate Chem.* 5:382–389 (1994); Remy et al., *Bioconjugate Chem.* 5:647–654 (1994); Gao et al., *Gene Therapy* 2:710–722 (1995); Ahmad et al., *Cancer Res.* 52:4817–4820 (1992); U.S. Pat. Nos. 4,186,183, 4,217,344, 4,235,871, 4,261,975, 4,485,054, 4,501,728, 4,774,085, 4,837,028, and 4,946, 787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6–10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., *J. Virol.* 66:2731–2739 (1992); Johann et al., *J. Virol.* 66:1635–1640 (1992); Sommerfelt et al., *J. Virol.* 176:58–59 (1990); Wilson et al., *J. Virol.* 63:2374–2378 (1989); Miller et al., *J. Virol.* 65:2220–2224 (1991); PCT/US94/05700).

In applications where transient expression of the nucleic acid is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38–47 (1987); U.S. Pat. No. 4,797,368; WO 93/24641; Kotin, *Human Gene Therapy* 5:793–801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251–3260 (1985); Tratschin, et al., *Mol. Cell. Biol.* 4:2072–2081 (1984); Hermonat & Muzyczka, *Proc. Natl. Acad. Sci. U.S.A.* 81:6466–6470 (1984); and Samulski et al., *J. Virol.* 63:03822–3828 (1989).

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., *Blood* 85:3048–305 (1995); Kohn et al., *Nat. Med.* 1:1017–102 (1995); Malech et al., *Proc. Natl. Acad. Sci. U.S.A.* 94:22 12133–12138 (1997)). PA317/pLASN was the first therapeutic vector used in a gene therapy trial. (Blaese et al., *Science* 270:475–480 (1995)). Transduction efficiencies of 50% or greater have been observed for MFG-S packaged vectors. (Ellem et al., *Immunol Immunother.* 44(1):10–20 (1997); Dranoff et al., *Hum. Gene Ther.* 1:111–2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702–3 (1998), Kearns et al., *Gene Ther.* 9:748–55 (1996)).

Replication-deficient recombinant adenoviral vectors (Ad) are predominantly used transient expression gene therapy, because they can be produced at high titer and they readily infect a number of different cell types. Most adenovirus vectors are engineered such that a transgene replaces the Ad E1, E1, and E3 genes; subsequently the replication defector vector is propagated in human 293 cells that supply deleted gene function in trans. Ad vectors can transduce multiply types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083–9 (1998)). Additional examples of the use of adenovirus vectors for gene transfer in clinical trials include Rosenecker et al., *Infection* 24:15–10 (1996); Sterman et al., *Hum. Gene Ther.* 9:7 1083–1089 (1998); Welsh et al., *Hum. Gene Ther.* 2:205–18 (1995); Alvarez el al., *Hum. Gene Ther.* 5:597–613 (1997); Topf et al., *Gene Ther.* 5:507–513 (1998); Sterman et al., *Hum. Gene Ther.* 7:1083–1089 (1998).

Packaging cells are used to form virus particles that are capable of infecting a host cell. Such cells include 293 cells, which package adenovirus, and ø2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *Proc. Natl. Acad. Sci. U.S.A.* 92:9747–9751 (1995), reported that Moloney murine leukemia virus can be modified to express human, heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., Fab or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-alpha and TNF-alpha are known (see Inaba et al., *J. Exp. Med.* 176:1693–1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panb cells), GR-1 (granulocytes), and Iad (differentiated antigen presenting cells) (see Inaba et al., *J. Exp. Med.* 176:1693–1702 (1992)).

Vectors (e.g., retroviruses, adenoviruses, liposomes, etc.) containing therapeutic nucleic acids can be also administered directly to the organism for transduction of cells in vivo. Alternatively, naked DNA can be administered.

Administration is by any of the routes normally used for introducing a molecule into ultimate contact with blood or tissue cells, as described below. The nucleic acids are administered in any suitable manner, preferably with pharmaceutically acceptable carriers. Suitable methods of administering such nucleic acids are available and well known to those of skill in the art, and, although more than one route can be used to administer a particular composition, a particular route can often provide a more immediate and more effective reaction than another route (see *Proc. Natl. Acad. Sci. U.S.A.* 81:6466–6470 (1984); and Samulski et al., *J. Virol.* 63:03822–3828 (1989)). In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

VIII. Pharmaceutical Compositions and Administration

LF and LF homologue nucleic acid and protein, PA protein, and modulators and mimetics of LF can be administered directly to the patient for inhibition of cancer, tumor, or precancer cells in vivo. Administration is by any of the routes normally used for introducing a compound into ultimate contact with the tissue to be treated. The compounds are administered in any suitable manner, preferably with pharmaceutically acceptable carriers. Suitable methods of administering such compounds are available and well known to those of skill in the art, and, although more than one route can be used to administer a particular composition, a particular route can often provide a more immediate and more effective reaction than another route. As described above, in one embodiment, LF and LF homologues are administered to a cell in the presence of PA or a targeted PA fusion protein.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, $17^{th}$ ed. 1985)).

The compounds (nucleic acids, proteins, and modulators), alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a patient, in the context of the present invention should be sufficient to effect a beneficial therapeutic response in the patient over time. The dose will be determined by the efficacy of the particular compound employed and the condition of the patient, as well as the body weight or surface area of the patient to be treated. The size of the dose also will be determined by the existence, nature, and extent of any adverse side-effects that accompany the administration of a particular compound or vector in a particular patient.

In determining the effective amount of the modulator to be administered in the treatment or prophylaxis of cancer, the physician evaluates circulating plasma levels of the modulator, modulator toxicities, progression of the disease, and the production of anti-modulator antibodies. In general, the dose equivalent of a modulator is from about 1 ng/kg to 10 mg/kg for a typical patient. Administration of compounds is well known to those of skill in the art (see, e.g., Bansinath et al., *Neurochem Res.* 18:1063–1066 (1993); Iwasaki et al., *Jpn. J. Cancer Res.* 88:861–866 (1997); Tabrizi-Rad et al., *Br. J. Pharmacol.* 111:394–396 (1994)).

For administration, modulators of the present invention can be administered at a rate determined by the LD-50 of the modulator, and the side-effects of the inhibitor at various concentrations, as applied to the mass and overall health of the patient. Administration can be accomplished via single or divided doses.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example 1

In vitro and ex vivo Inhibition of Mos Activation of Maturation Promoting Factor The activity of anthrax lethal toxin as an inhibitor of the MAPK signal transduction pathway can be examined in *Xenopus* oocyte extracts. Activation of the MAPK pathway by newly synthesized Mos is essential for the activation of maturation promoting factor (i.e., cyclin B/p34$^{cdc2}$ kinase) and the resumption of meiosis (maturation) in oocytes (see Murakami et al., *Methods in Enzymology* 283:584–600 (Dunphy, ed., 1991)). Accordingly, the effect of lethal factor was assayed by examining inhibition of Mos activation of oocyte maturation, using oocyte extracts and direct injection of LF into oocytes.

a. Ex vivo Inhibition

For the ex vivo assays, *Xenopus* oocytes were isolated, defolliculated, injected, and induced to mature with progesterone as described previously (Duesbery et al., *Proc. Natl. Acad. Sci. USA* 94:9165–9170 (1997)). LF and PA were purified from culture supernatants of *B. anthracis* Sterne, a strain that produces PA, LF, and EF, using methods described previously (Leppla, in *Methods in Enzymology* 165:103–116 (Harshman, ed., 1988)). PA and LF were either added to oocyte culture medium, or LF was directly injected into oocytes.

Addition of FPLC-purified PA and LF, prepared from *B. anthracis* Sterne, to oocyte culture medium had no effect on oocyte maturation. By contrast, injection of LF into oocytes potently inhibited progesterone-induced maturation (Table 1). Injection of as little as 1 ng LF inhibited maturation by 50% as judged by assay of germinal vesicle (i.e., nuclear envelope) breakdown (GVBD), and GVBD was completely inhibited by 10 ng LF. To assay GVBD breakdown, oocytes were fixed in formalin fixative and manually dissected with a scalpel to determine whether the germinal vesicle was still intact (Duesbery & Masui, *Dev. Genes Evol.* 206:110–124 (1996)). The injection of the inactive LF mutant, LF E687C, had no effect upon GVBD (Table 1). Preparations of LF from strains of *B. anthracis* deficient in the production of EF also blocked oocyte maturation (Table 1). The inhibitory effects of LF upon progesterone-induced GVBD were reversible since the subsequent injection of Δ90 cyclin B, a truncated, non-degradable form of cyclin B (Glotzer et al., *Nature* 349:132–138 (1991)) could induce GVBD (Table 1).

TABLE 1

LF blocks oocyte maturation

| Material injected | progesterone treatment | GVBD (#frogs used) |
|---|---|---|
| none | − | 0/128 (7)[†] |
| none | + | 143/158 (7)[†] |
| injection buffer[‡] | + | 61/75 (4)[†] |
| 1 ng LF | + | 24/52 (3)[†] |
| 10 ng LF | + | 0/50 (3)[†] |
| 40 ng LF | + | 0/75 (4)[†] |
| 40 ng LF(E687C) | + | 57/73 (4)[†] |
| none | − | 0/99 (3)[¶] |
| none | + | 108/113 (3)[¶] |
| 40 ng LF[∥] | + | 0/75 (3)[¶] |
| 24 ng Δ90 cyclin | − | 43/43 (2)[¶] |
| 40 ng LF[∥], 24 ng Δ90 cyclin | − | 75/75 (3)[¶] |

[†]Scored by dissection at 20 hours post progesterone treatment.
[‡]0.1 M KCL, 10 mM Hepes, pH 7.5.
[∥]LF was produced as a recombinant fusion protein, PA20-LF, and cleaved with Factor X to release the PA20 domain (Klimpel et al., Mol. Microbial. 13: 1093–1100 (1994)). The expression host was *B. anthracis* lacking the EF gene.
[¶]Scored by dissection at 4 hours post progesterone treatment, when GVBD was completed in control oocytes.

b. In vitro Inhibition

The oocyte extract assay was performed as follows. LF or LF mutant E687C (4 μg from a 1 mg/mL stock) was added to 40 μl oocyte lysate (Shibuya et al., *EMBO J.* 11:3963–3975 (1992)). LF E867C is an inactive LF mutant described in Klimpel et al., *Mol. Microbiol.* 13:1093–1100 (1994). Lysates were activated 0.5 hr later by the addition of 2.6 μg maltose binding protein-Mos fusion protein (0.75 mg/mL stock). Mos with wild type activity was purified from bacteria as a malE mos$^{Xe}$ fusion product (Yew et al., *Nature* 355:649–652 (1992)). Aliquots were taken at 1 hr intervals and frozen for later analysis by SDS-PAGE and western blotting (Duesbery et al., *Proc. Natl. Acad. Sci. USA* 94:9165–9170 (1997)). Blots were probed with antibodies raised against phosphorylated MAPK (PO$_4$-MAPK) (New England Laboratories, 1:1000), MAPK (Zymed clone ERK-7D8, 1:1000), the C-terminus of MAPPKL (MAPKK1 (Ct)) (Upstate Biotechnology, 1:500), or the N-terminus of MAP-PKL (MAPKK1 (Nt)) (Upstate Biotechnology, 1:500) and visualized by chemiluminescence with HRP-conjugated secondary antibodies.

The addition of LF, but not LF E687C, inhibited Mos-induced activation of MAPK in oocyte lysates, suggesting that oocytes are unable to mature in the presence of LF due to a failure in MAPK activation. When western blots of these lysates were probed with antibodies to the C-terminus of MAPKK1, antigen was detected throughout the incubation (albeit at reduced levels when compared to control lysates), whereas, if probed with antibodies to the N-terminus of MAPKK1, the antigen was not detected at any time after the addition of LF.

These results revealed that LF modifies MAPKK1, rendering the protein undetectable by antibodies raised against its N-terminus. Indeed, in the presence of LF, the mobility of MAPKK1 observed with the C-terminal antibody increased slightly, suggesting that MAPKK1 was proteolytically modified.

Example II

Activity of LF in Cells that Have an Activated MAPK Pathway

The effects of LF were tested upon tumor-derived NIH3T3 (490) cells expressing an effector domain mutant form of the human V12HaRas oncogene (V12-S35 Hras). This oncogenic mutant of Ras retains constitutive activation of the Raf-MAPKK-MAPK pathway, but is defective in other effector functions (White et al., *Cell* 80:533–541 (1995)). Cells transformed with this Ras mutant are tumorigenic, and derived tumors display high levels of MAPK (ERK ½) activity. These cells were used instead of wild type V12HRas transformed cells to eliminate the possibility of MEK-independent pathways contributing to ERK ½ activity.

The NIH3T3 cells expressing an effector domain mutant form of the human V12HaRas oncogene (V12-S35 Hras) were grown in 6-well plates to approximately 70% confluence in DMEM+10% FBS. Cells were then incubated in fresh DMEM+10% FBS containing 1 μg/mL of PA for 10 min. Control media, LF, or, LF E687C was then added directly to the cells at a final concentration of 0.1 μg/mL. Cells were lysed (at 20 min., 1 hr. or 3 hrs.) in lysis buffer (20 mM Pipes, pH 7.4, 150 mM NaCl, 1 mM EGTA, 1.5 mM $MgCl_2$, 1% SDS, 10 μg/mL aprotonin and leupeptin, 1 mM PMSF, 1 mM sodium orthovanadate) and cell lysates were clarified by centrifugation (15,000 g for 15 min., 4° C.). Protein concentrations in clarified cell lysates were determined using the Pierce BCA protein determination kit and samples (10 μg) were analyzed by SDS-PAGE and western blotting as described above with the exception that antibodies raised against phosphorylated MAPK were obtained from Promega (1:15,000).

The addition of PA and LF, but not LF E687C, to these cells inhibited MAPK activation. This inhibition was also accompanied by an increase in the electrophoretic mobility of MAPKK1 observed with the C-terminal antibody, as well as a loss of MAPKK1 epitopes observed with the N-terminal antibody, further demonstrating that LF proteolytically modifies MAPKK1.

Example III

In vitro Assay for LF Activity Using MBP Phosphorylation

The effects of LF upon MAPK activation were directly demonstrated by assaying, in vitro, myelin basic protein (MBP) phosphorylation in the presence of MAPKK1 and MAPK (ERK 2).

His-tagged MAPKK1, possessing endogenous activity (0.25 μg from a 0.1 mg/mL stock prepared from bacterial lysates) was diluted in 16 μL assay buffer (composed of (1) 8 μL assay dilution buffer (ADB, Upstate Biotechnology; 20 mM MOPS, pH 7.2, 25 mM β-glycerophosphate, 5 mM EGTA, 1 mM sodium orthovanadate, 1 mM dithiothreitol); and (2) 8 μL inhibitor cocktail (Upstate Biotechnology; 20 mM PKC inhibitor peptide, 2 mM protein kinase A inhibitor peptide, and 20 mM compound R24571 in ADB)); and incubated for 15 min. at 30° C. in the presence or absence of 0.25 μg LF or LF E687C.

After incubation, samples were added to 11 μL kinase buffer, composed of: 0.35 μg Erk2 (from a 0.35 mg/ml stock); $(His)_6$-tagged (SEQ ID NO:10) MAPK (expressed in bacterial cells obtained from Drs. Cobb and Robbins, and purified as described by Robbins, et al., *J. Biol Chem.* 268:5097–5106 (1993); 10 μg myelin basic protein (MBP) (Upstate Biotechnology 5 mg/ml); and 8 μL Mg/ATP solution (($\gamma$-$^{32}$P)-ATP (Amersham; 10 mCi/ml, 3000 mCi/mmol) diluted 1:9 in 0.5 mM ATP, 75 mM $MgCl_2$ in ADB). After 15 min. incubation at 30° C., samples were separated by SDS-PAGE upon 14% gels and processed for autoradiography.

The addition of LF, but not LF E687C, prevented MBP phosphorylation. Thus, as seen ex vivo, LF directly inhibits MAPK activation in vitro.

To exclude the possibility that contaminants in the LF preparation may be responsible for the inhibition of MBP phosphorylation, LF was adsorbed to the PA63 heptamer, to which it tightly binds (Singh et al., *J. Biol. Chem.* 269:29039–29046 (1995)), and re-purified by column chromatography, as follows.

LF previously purified by hydroxylapatite and ion exchange chromatography was re-chromatographed on a MonoQ HR5/5 column in the presence and absence of the PA63 heptamer. The MonoQ column was eluted with a gradient of NaCl in 10 mM CHES, 0.06% aminoethanol, pH 9.0. The samples applied to the columns were 250 μg LF, 250 μg PA63, and 250 μg LF+350 μg PA63. Fractions were pooled and assayed for inhibition of MAPKK1 activity as described above. Lane 1, LF alone (fractions 18–23); lanes 2, 3 and 4, PA63 alone (fractions 18–23 (lane 2), 24–29 (lane 3), and 27–28 (lane 4)); lanes 5, 6 and 7, PA63 & LF (fractions 18–23 (lane 5 24–29 (lane 6), and 27–28 (lane 7)). Western blotting confirmed that all the LF protein bound to the PA63 heptamer and eluted in peaks 6 & 7.

In all cases, the inhibition of MBP phosphorylation was found to co-elute with LF. MAPKK1 inhibitory activity therefore co-migrates with LF repurified by adsorption to PA63.

Example IV

Assay In vitro for LF MAPKK Activity Using Changes in MAPKK1 Electrophoretic Mobility Direct testing for LF cleavage of MAPKK1 was performed by examining the increase in electrophoretic mobility of MAPKK1 and the disappearance of N-terminal epitopes in vitro. This assay was performed using a $His_6$-tagged (SEQ ID NO:10) MAPKK1 fusion protein produced in bacteria.

The assay was performed as follows. His-tagged MAPKK1 (0.1 μg) was incubated in 16 μl assay buffer, as described above, in the presence of 1 μg LF E687C (lanes 1–3) or 1 μg LF (lanes 4–6). Samples were withdrawn at 0, 10, or 20 min. and analyzed by SDS-PAGE and western blotting with antibodies raised against the C-terminus of MAPKK1.

This experiment demonstrated that, within seconds of LF addition, the apparent $M_r$ of MAPKK1 decreased by approximately 6–8 kDa. Furthermore, cleavage by LF is enzymatic, since LF proteolysis of MAPKK1 was observed within 15 min with as little as 2 ng LF per 200 ng MAPKK1 (approximately 1 mol LF: 400 mol MAPKK1).

To demonstrate that cleavage by LF is enzymatic, $His_6$ (SEQ ID NO:10)-MAPKK1 (0.2 μg) was incubated as described above in the presence of 2 μg LF E687C (lane 1) or LF (lanes 2–6), which had been serially diluted in ADB (2 μg to 0.2 ng). Aliquots were withdrawn at the 15 and 30 min. time points and analyzed by SDS-PAGE and western blotting with antibodies raised against the C-terminus of MAPKK1.

Since the MAPKK1 used in these analyses is His-6-tagged at the N-terminus (Mansour et al., *Cell Growth and Differ.* 7:243–250 (1996)), the actual decrease in the $M_r$ of MAPKK1 is approximately 5 kDa less (Mansour et al., *Cell Growth and Differ.* 7:243–250 (1996)), suggesting that LF cleaves MAPKK1 in the first 30 amino acids.

Example V

Determination of MAPKK Cleavage Site for LF

To determine where LF cleaves MAPKK1, previously prepared N-terminal deletion mutants of MAPKK1

(Mansour et al., *Science* 265:966–970 (1994)) were assayed for their ability to serve as substrates for LF, as follows.

His-tagged MAPKK1 deletion mutants (0.1 μg) were isolated from bacterial lysates as described (Mansour et al., *Science* 265:966–970 (1994), were incubated in assay buffer as described in the presence or absence of LF (1 μg) for 15 min. at 30° C., and were analyzed by SDS-PAGE and western blotting as described above. MAPKK1 deletion mutants ΔN1 and ΔN2 were completely resistant to proteolysis, whereas ΔN3, Δ4, and Δ6 were cleaved. ΔN5 showed partial resistance to proteolysis, suggesting that structural modifications in this construct may partially hinder LF activity.

These analyses showed that ΔN3 (32–51), ΔN4 (44–51), ΔN5 (3843), and ΔN6 (32–37) were susceptible to LF proteolysis whereas ΔN1 (1–32) and ΔN2 (1–52) were not. Thus, the N-terminal 32 amino acids are essential for cleavage and/or binding of MAPKK1 by LF.

Example VI

Identification of LF Cleavage Site on MAPKK1

To determine the exact site of LF cleavage of MAPKK1, N-terminal sequence analysis of the larger MAPKK1 proteolytic fragment was performed as described above.

MAPKK1 deletion mutants (0.1 μg) were incubated with LF (0.2 μg) as described for 30 min at 30° C., after which samples were separated by SDS-PAGE and blotted onto PVDF membrane in CAPS transfer buffer (3-[cyclohexylaminol-1 propanesulfonic acid (10 mM, pH 11), 10% methanol) at 300 mA constant current for 30 min. Following transfer, membranes were quickly stained with Ponceau S solution (0.1% Ponceau S, 5% acetic acid) and rinsed with distilled, deionized water.

For sequence analysis, the appropriate band was cut from the membrane and subjected to automated Edman degradation in an Applied Bio systems 477A gas-phase sequencer and phenylthiohydantoin derivatives were identified on line with a 120 phenylthiohydantoin analyzer.

After sequence analysis, the amino acid sequence IQLN-PAPDG (SEQ ID NO:11) was identified, which corresponds to amino acids 8–16 of MAPKK1. Thus, LF cleaves MAPKK1 between amino acids 7 and 8, resulting in the loss of the N-terminal seven residues (PKKKPTP; SEQ ID NO:12). Consistent with the ex vivo and in vitro assays, previous analysis of MAPKK1 deletion mutants has indicated that mutants with deletions of the N-terminal 32 amino acids possess less activity than wild-type MAPKK1 (Mansour et al., *Biochemistry* 35:15529–15536 (1996)). In addition, the N-terminal 32 amino acids of MAPKK1 contain a MAPK binding site (Fukuda et al., *EMBO J*. 16:1901–1908 (1997)), suggesting that LF may prevent the association of MAPKK1 with its substrate. These results demonstrate that the seven N-terminal residues of MAPKK1 are essential for its activity. MAPKK1 prolines 5 and 7 were each separately mutated to an alanine in two MAPKK1 mutants. Both mutants were resistant to LF cleavage, indicating that these proline residues may be an important component of the cleavage site.

As observed for MAPKK1, the electrophoretic mobility of MAPKK2 increased with LF treatment. Sequence analysis was performed for the N-terminus of the larger MAPKK2 proteolytic fragment. LF cleaved MAPKK2 between residues 9 and 10, resulting in the loss of N-terminal residues 1 to 9 (LARRKPVLP; SEQ ID NO:13). LF also cleaves MAPKK3.

The results presented above show that frog, mouse, and human MAPKK1, as well as human MAPKK2 and MAPKK3, are all substrates of LF (see FIG. 1).

Example VII

Effects of LF and PA on V12-H-ras Transformed Cells

NIH3T3 cells transformed with V12H-ras exhibit characteristics typical of transformed cells, including a distinct morphology, an ability to form foci very rapidly, a diffuse actin staining pattern, a rapid proliferation rate, and an ability to grow independent of anchorage to a substrate. As described infra, LF and PA can reverse each of these properties of V12H-ras transformed cells, restoring to the cells properties typical of normal, non-transformed cells.

a. Morphological Changes

Cells transformed with human H-ras (V12) have a distinct appearance characterized by long, spindle-shaped cells and an ability to form foci very rapidly. To assess the ability of PA and LF to reverse these morphological features, NIH3T3 (490) cells expressing human H-ras (V12) protein were grown in DMEM supplemented with 10% fetal bovine serum, 2% penicillin/streptomycin, and maintained at 37° C. in a humidified atmosphere of 10% $CO_2$, and with or without the presence of PA and LF. After 24 hours in the presence of PA and LF, the transformed cells lost the distinct appearance described above and assumed a flatter, larger appearance typical of non-transformed cells. Further, cells grown in the presence of PA and LF failed to form foci. In contrast, cells grown in the presence of PA alone, or PA and LF E687C, failed to undergo any morphological changes.

Another characteristic feature of H-ras (V12) transformed cells is a diffuse pattern of actin staining. To assess whether PA and LF were able to restore a normal, non-transformed pattern of actin distribution to the transformed NIH3T3 cells, the cells were stained for actin and examined using a confocal microscope. Cells were grown on 4 well glass slides (Nunc, Ill.), washed twice with PBS, and fixed with methanol for 15 minutes at 4° C. After the methanol was removed, cells were air-dried and then rehydrated with PBS for 5 minutes. Cells were then post-fixed with 4% formalin for 15 minutes, washed with PBS and permeabilized with 1% NP40 in PBS for 5 minutes. After rinsing, cells were incubated with blocking solution antibody (PBS containing 10% normal goat serum, 3% BSA, 0.1% Tween-20) for 1 hour at 37° C. The cells were then incubated with mouse monoclonal anti-actin (Sigma, clone KJ43A; 1:250) (in blocking solution) for 1 hour at room temperature. The antigen-antibody complexes were detected with Texas red conjugated anti-mouse IgG antibody (Molecular probes; 1:250) for 30 minutes at room temperature and rinsed three times. Coverslips were mounted in aqueous non-fluorescing medium containing 1 mg/ml Hoechst 33342. Slides were then examined by confocal laser scanning microscopy.

Transformed cells grown in the absence of LF and PA displayed, as described above, a diffuse pattern of actin staining. In contrast, in transformed cells treated with PA and LF, the actin was organized into "stress fibers" typical of non-transformed cells. Transformed cells grown in the presence of PA alone, or PA and LF E687C, failed to show any changes in actin distribution.

b. Cell Cycle

To determine whether the presence of LF and PA can inhibit the rapid proliferation characteristic of transformed cells, transformed cells were incubated, as described supra, in the presence or absence of LT for 0–7 days. Analysis of the proliferation rate of the cells demonstrated that LT inhibited the proliferation of the cells. To determine the cell cycle stage affected by LT-mediated inhibition, the cells were analyzed for cell cycle distribution by flow cytometry using the Cellular DNA Flow Cytometric analysis reagent set (Boehringer Mannheim, Ind.). At various sampling points, medium was collected and combined with trypsinized cells and centrifuged at 2000 rpm for 5 minutes in a Beckmann GS-6R centrifuge at 4° C. The resulting pellet was washed once with cold Versene 1:5000 (Gibco-BRL, NewYork) and fixed in 70% ethanol for 30 minutes at 4° C. Cells were then spun down and rehydrated in 1 ml PBS ($-Ca^{2+}/M^{2+}$) at room temperature for 30 minutes, at which point 10 ml FCS was added and cells were incubated for 30 additional minutes. Cells were then spun down and incubated in 1 ml PBS ($-Ca^{2+}/Mg^{2+}$) including 5 ml RNAse (DNAse free) and 100 ml propidium iodide at room temperature for 30 minutes. Samples were then subjected to flow cytometric analysis. This analysis of the cells by fluorescence activated cell sorting indicated that treatment with LT caused the cells to arrest at G1 phase of the cell cycle.

c. Anchorage-Independent Growth

Another hallmark of the transformed cell is its ability to grow independent of its anchorage to a substrate and to invade other tissues. These characteristics may be assayed in vitro by monitoring the ability of single cell suspensions to proliferate in soft agar or to 'branch' while suspended in medium that mimics the extracellular environment of the cell, e.g., Matrigel. To assess the ability of LT to reverse these properties, ras-transformed NIH3T3 cells were grown in the presence or absence of LT and assayed for the above-described properties.

Three-dimensional Matrigel invasion assays were performed as described previously (Jeffers et al., *Mol. Cell. Biol.* 16:1115 (1996)) with modification. Cells were collected by centrifugation after incubation in PBS containing 0.2 g/L EDTA (Versene, Gibco BRL) at 37° C. for 0.5 hours. Approximately $2.5 \times 10^4$ cells in a volume of 62.5 ml DMEM, 10% fetal bovine serum, were mixed with an equal volume of non-diluted GFR-Matrigel (see, e.g., Martin et al,. *Hum. Reprod.* 13:1645 (1998)) supplemented with or without PA (1 mg/ml) or LF (E687C) (0.01–1 mg/ml). The cell suspension was then added to a 96-well culture plate and incubated 0.5 hours at 37° C., 10% $CO_2$, to solidify. DMEM containing 10% calf serum was then layered overtop and the cells were further incubated at 37° C., 5% $CO_2$ for up to one week, during which cells were monitored daily. Each sample was assayed in triplicate in three separate experiments. In these experiments, the presence of LT prevented the transformed cells from undergoing branching morphogenesis in the Matrigel.

For soft agar colony formation assays, trypsinized cells were washed with $Ca^{2+}/Mg^{2+}$-free PBS, resuspended at a concentration of $1 \times 10^4$ cells/ml in DMEM containing 10% calf serum, 0.5% (W/V) Noble agar (Difco laboratories, Mich.), in the presence or absence of LT, and layered over a 0.5 ml solid plug of DMEM containing 1% agar in 24 well plates. It was observed that cells grown in the absence of LT were capable of proliferating in the agar, in contrast to cells grown in the presence of LT, which were prevented from proliferating in the agar.

The above results demonstrate that LT can reverse multiple aspects of the transformed phenotype, including morphological features, proliferation, and anchorage-independent growth.

What is claimed is:

1. A method for inhibiting proliferation of cancer cell, the method comprising the step of contacting the cell with *Bacillus anthratics* lethal factor (LF), wherein the LF has mitogen activated kinase kinase (MAPKK) protease activity, and wherein the mitogen activated protein kinase (MAPK) signal transduction pathway is activated in the cancer cell [has an activated MAPKK signal transduction pathway].

2. The method of claim 1, wherein LF is recombinant.

3. The method of claim 1, wherein the step of contacting the cell comprises transducing the cell with an expression vector encoding LF.

4. The method of claim 1, wherein the step of contacting the cell with LF comprises contacting the cell with LF in the presence of protective antigen.

5. The method of claim 4, wherein the PA is a fusion protein targeted to the cancer cell.

6. The method of claim 1, wherein the cell is a human cell.

7. The method of claim 1, wherein the cancer cell is from a sarcoma.

8. The method of claim 1, wherein the cell is from a transformed cell line.

9. The method of claim 8, wherein the cell line is transformed with Ras.

10. The method of claim 1, wherein the cell is in a mammal.

* * * * *

SEQUENCE LISTING

<160> NUMBER OF SEQ ID NOS: 13

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:primer used
      to amplify a sequence of Bacillus anthracis anthrax
      toxin lethal factor (LF)

<400> SEQUENCE: 1
cctaagggca cagcaaagaa tgag                                          24

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:primer used
      to amplify a sequence of Bacillus anthracis anthrax
      toxin lethal factor (LF)

<400> SEQUENCE: 2
gtgtggcgaa agtggtggtc                                               20

<210> SEQ ID NO 3
<211> LENGTH: 5
<212> TYPE: PRT
<213> ORGANISM: Artificial Sequence -continued

```
<220> FEATURE:
<223> OTHER INFORMATION: Description of Artificial Sequence:putative
      zinc-binding site at residues 686-690 of anthrax
      toxin lethal factor (LF)

<400> SEQUENCE: 3

His Glu Phe Gly His
 1               5

<210> SEQ ID NO 4
<211> LENGTH: 50
<212> TYPE: PRT
<213> ORGANISM: Artificial Sequence
<220> FEATURE:
<223> OTHER INFORMATION: Description of Artificial Sequence:N-terminal
      amino acids of Xenopus mitogen activated protein
      kinase kinase 1 (MAPKK1)

<400> SEQUENCE: 4

Pro Lys Lys Lys Pro Thr Pro Ile Gln Leu Asn Pro Asn Pro Glu Gly
 1               5                  10                  15

Thr Ala Val Asn Gly Thr Pro Thr Ala Glu Thr Asn Leu Glu Ala Leu
            20                  25                  30

Gln Lys Lys Leu Glu Glu Leu Glu Leu Asp Glu Gln Gln Arg Lys Arg
        35                  40                  45

Leu Glu
    50

<210> SEQ ID NO 5
<211> LENGTH: 51
<212> TYPE: PRT
<213> ORGANISM: Artificial Sequence
<220> FEATURE:
<223> OTHER INFORMATION: Description of Artificial Sequence:N-terminal
      amino acids of mouse mitogen activated protein
      kinase kinase 1 (MAPKK1)

<400> SEQUENCE: 5

Pro Lys Lys Lys Pro Thr Pro Ile Gln Leu Asn Pro Ala Pro Asp Gly
 1               5                  10                  15

Ser Ala Val Asn Gly Thr Ser Ser Ala Glu Thr Asn Leu Glu Ala Leu
            20                  25                  30

Gln Lys Lys Leu Glu Glu Leu Glu Leu Asp Glu Gln Gln Arg Lys Arg
        35                  40                  45

Leu Glu Asp
    50

<210> SEQ ID NO 6
<211> LENGTH: 50
<212> TYPE: PRT
<213> ORGANISM: Artificial Sequence
<220> FEATURE:
<223> OTHER INFORMATION: Description of Artificial Sequence:N-terminal
      amino acids of human mitogen activated protein
      kinase kinase 1 (MAPKK1)

<400> SEQUENCE: 6

Pro Lys Lys Lys Pro Thr Pro Ile Gln Leu Asn Pro Ala Pro Asp Gly
 1               5                  10                  15

Ser Ala Val Asn Gly Thr Ser Ser Ala Glu Thr Asn Leu Glu Ala Leu
            20                  25                  30

Gln Lys Lys Leu Glu Glu Leu Glu Leu Asp Glu Gln Gln Arg Lys Arg
        35                  40                  45
```

-continued

Leu Glu
    50

<210> SEQ ID NO 7
<211> LENGTH: 49
<212> TYPE: PRT
<213> ORGANISM: Artificial Sequence
<220> FEATURE:
<223> OTHER INFORMATION: Description of Artificial Sequence:N-terminal
      amino acids of human mitogen activated protein
      kinase kinase 2 (MAPKK2)

<400> SEQUENCE: 7

Leu Ala Arg Arg Lys Pro Val Leu Pro Ala Leu Thr Ile Asn Pro Thr
 1               5                  10                  15

Ile Ala Glu Gly Pro Ser Pro Thr Ser Glu Gly Ala Ser Glu Ala Asn
            20                  25                  30

Leu Val Asp Leu Gln Lys Lys Leu Glu Glu Leu Glu Leu Asp Glu Gln
        35                  40                  45

Gln

<210> SEQ ID NO 8
<211> LENGTH: 49
<212> TYPE: PRT
<213> ORGANISM: Artificial Sequence
<220> FEATURE:
<223> OTHER INFORMATION: Description of Artificial Sequence:N-terminal
      amino acids of human mitogen activated protein
      kinase kinase 3 (MAPKK3)

<400> SEQUENCE: 8

Ser Lys Pro Pro Ala Pro Asn Pro Thr Pro Pro Arg Asn Leu Asp Ser
 1               5                  10                  15

Arg Thr Phe Ile Thr Ile Gly Asp Arg Asn Phe Glu Val Glu Ala Asp
            20                  25                  30

Asp Leu Val Thr Ile Ser Glu Leu Gly Arg Gly Ala Tyr Gly Val Val
        35                  40                  45

Glu

<210> SEQ ID NO 9
<211> LENGTH: 49
<212> TYPE: PRT
<213> ORGANISM: Artificial Sequence
<220> FEATURE:
<223> OTHER INFORMATION: Description of Artificial Sequence:N-terminal
      amino acids of human mitogen activated protein
      kinase kinase 4 (MAPKK4)

<400> SEQUENCE: 9

Ala Ala Pro Ser Pro Ser Gly Gly Gly Gly Ser Gly Gly Gly Ser Gly
 1               5                  10                  15

Ser Gly Thr Pro Gly Pro Val Gly Ser Pro Ala Pro Gly His Pro Ala
            20                  25                  30

Val Ser Ser Met Gln Gly Lys Arg Lys Ala Leu Lys Leu Asn Phe Ala
        35                  40                  45

Asn

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:(His)6 tag -continued

<400> SEQUENCE: 10

His His His His His His
1 5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence:amino acids 8-16 of Xenopus MAPKK1

<400> SEQUENCE: 11

Ile Gln Leu Asn Pro Ala Pro Asp Gly
1 5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:N-terminal 7 amino acid residues of Xenopus MAPKK1

<400> SEQUENCE: 12

Pro Lys Lys Lys Pro Thr Pro
1 5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:N-terminal amino acid residues 1-9 of MAPKK2

<400> SEQUENCE: 13

Leu Ala Arg Arg Lys Pro Val Leu Pro
1 5